United States Patent
Arditi et al.

(10) Patent No.: US 8,496,591 B2
(45) Date of Patent: Jul. 30, 2013

(54) PERFUSION ASSESSMENT METHOD AND SYSTEM BASED ON BOLUS ADMINISTRATION

(75) Inventors: Marcel Arditi, Genève (CH); Peter Frinking, Genèva (CH); Nicolas Rognin, Genève (CH)

(73) Assignee: Bracco Suisse S.A., Manno (CH)

( * ) Notice: Subject to any disclaimer, the term of this patent is extended or adjusted under 35 U.S.C. 154(b) by 1404 days.

(21) Appl. No.: 11/794,182

(22) PCT Filed: Dec. 21, 2005

(86) PCT No.: PCT/EP2005/057065
§ 371 (c)(1),
(2), (4) Date: Jun. 25, 2007

(87) PCT Pub. No.: WO2006/067201
PCT Pub. Date: Jun. 29, 2006

(65) Prior Publication Data
US 2008/0228080 A1    Sep. 18, 2008

(30) Foreign Application Priority Data
Dec. 23, 2004 (EP) .................................. 04106962

(51) Int. Cl.
*A61B 8/14* (2006.01)
*G06K 9/00* (2006.01)

(52) U.S. Cl.
USPC .......................................... 600/458; 382/128

(58) Field of Classification Search
None
See application file for complete search history.

(56) References Cited

U.S. PATENT DOCUMENTS

| 5,860,931 | A | 1/1999 | Chandler |
| 6,080,107 | A | 6/2000 | Poland |
| 6,149,597 | A | 11/2000 | Kamiyama |
| 6,315,730 | B1 | 11/2001 | Hoff et al. |

(Continued)

FOREIGN PATENT DOCUMENTS

| EP | 0458745 | 11/1991 |
| EP | 0554213 | 4/1993 |

(Continued)

OTHER PUBLICATIONS

International Search Report for International Patent Application Serial No. PCT/EP2005/057065; European Patent Office, Oct. 25, 2006.

(Continued)

*Primary Examiner* — Long V. Le
*Assistant Examiner* — Angela M Hoffa
(74) *Attorney, Agent, or Firm* — Bryan A. Santarelli; Graybeal Jackson LLP

(57) ABSTRACT

A perfusion assessment system is proposed. The system includes means for providing an echo-power signal indicative of a perfusion of a contrast agent in a body-part under analysis, the contrast agent being administered as a bolus and undergoing a significant destruction during a passage of the contrast agent in the body-part, means for associating the echo-power signal to a model function including the product between a bolus function indicative of the passage of the contrast agent without said destruction and a reperfusion function indicative of a reperfusion of the contrast agent in the body part following the destruction corresponding to a substantially constant inflow of the contrast agent, and means for estimating at least one perfusion indicator from the bolus function and/or the reperfusion function.

20 Claims, 8 Drawing Sheets

U.S. PATENT DOCUMENTS

| | | | |
|---|---|---|---|
| 6,461,303 | B2 | 10/2002 | Angelsen |
| 6,547,738 | B2 | 4/2003 | Lysyansky |
| 7,054,454 | B2 | 5/2006 | Causevic et al. |
| 7,415,142 | B2 | 8/2008 | Breeuwer |
| 7,753,850 | B2 | 7/2010 | Averkiou et al. |
| 8,021,303 | B2 | 9/2011 | Frinking et al. |
| 2002/0029130 | A1 | 3/2002 | Eryurek et al. |
| 2002/0040189 | A1 | 4/2002 | Averkiou et al. |
| 2003/0092991 | A1 | 5/2003 | Sehgal |
| 2003/0114759 | A1 | 6/2003 | Skyba et al. |
| 2003/0185408 | A1 | 10/2003 | Causevic et al. |
| 2006/0161062 | A1* | 7/2006 | Arditi et al. ............. 600/443 |
| 2008/0228080 | A1 | 9/2008 | Arditi et al. |
| 2008/0294027 | A1* | 11/2008 | Frinking et al. ............ 600/363 |

FOREIGN PATENT DOCUMENTS

| | | |
|---|---|---|
| WO | 9115244 | 10/1991 |
| WO | 9409829 | 5/1994 |
| WO | 9516467 | 6/1995 |
| WO | 02056666 | 7/2002 |
| WO | 02102251 | 12/2002 |
| WO | 2004110279 | 12/2004 |
| WO | 2006067201 | 6/2006 |
| WO | 2006067203 | 6/2006 |

OTHER PUBLICATIONS

International Search Report for International Patent Application Serial No. PCT/EP2004/051090; European Patent Office, Oct. 1, 2004.

International Search Report for International Patent Application Serial No. PCT/EP2005/057068; European Patent Office, Mar. 20, 2006.

Wei, Kevin, Jayaweera, Ananda R., Firoozan, Soroosh, Linka, Andre, Skyba, Danny M. and Kaul, Sanjiv "Quantification of Myocardial Blood Flow With Ultrasound-Induced Destruction of Microbubbles Administered as a Constant Venous Infusion", Journal of the American Heart Association Circulation 1998; vol. 5, No. 97; 473-483.

Byrd, Richard H., Schnabel, Robert B., Schultz, Gerald A., "Approximate Solution of the Trust Region Problem by Minimization Over Two-Dimensional Subspaces", University of Colorado at Boulder, Department of Science, 1988.

Coleman, Thomas F., Li, Yuying, "An Interior Trust Region Approach for Nonlinear Minimization Subject to Bounds"; Siam J. Optimization, Society for Industrial and Applied Mathematics; vol. 6, No. 2, pp. 418-445, May 1996.

Coleman, Thomas F., Li, Yuying, "On the convergence of Interior-reflective Newton Methods for Nonlinear Minimization Subject to Bounds"; The Mathematical Programming Society, Inc. 1994 p. 189-224.

Wei, Kevin, "Detection and Quantification of Coronary Stenosis Severity with Myocardial Contrast Echocardiography" Progress in Cardiovascular Diseases, vol. 44, No. 2, Sep. 10, 2001; p. 81-100.

Wei, Kevin, Le, Elizabeth, Bin, Jian-Ping, Coggins, Matthew, Thorpe, Jerrel, Kaul, Sanjiv, "Quantification of Renal Blood Flow with Contrast-Enhanced Ultrasound"; Journal of the American College of Cardiology; vol. 37 No. 4 2001; p. 1135-1140.

Kharchakdjian, Raffi, Burns, Peter N., Henkelman, Mark; "Fractal Modeling of Microbubble Destruction-reperfusion in Unresolved Vessels"; 2001 IEEE Ultrasonics Symposium p. 1669-1673.

Rim, Se-Joong, Poi-Leong, Howard, Lindner, Jonathan R., Couture, Daniel, Ellegala, Dilantha, Mason, Holland, Durieux, Marcel, Kassel, Neal F., Kaul, Sanjiv; "Quantification of Cerebral Perfusion with "Real-Time" Contrast-Enhanced Ultrasound"; Journal of the American Heart Association Circulation 2001; 104;p. 2582-2581.

Schlosser, Thomas, Pohl, Christoph, Veltmann, Christian, Lohmaier, Stefan, Goenechea, Jon, Ehlgen, Alexander, Koster, Jorg, Bimmel, Dieter, Kuntz-Hehner, Stefanie, Becher, Harald, Tiemann, Klaus; "Feasibility of the Flash-Replenishment Concept in Renal Tissue: Which Parameters Affect the Assessment of the Contrast Replenishment"; Ultrasound in Med & Biol., vol. 27, No. 7,p. 937-944 2001.

Murthy, Thippeswamy H., Li, Peng, Locvicchio, Elizabeth, Baish, Cheryl, Dairywala, Ismail, Armstrong, William F., Vannan, Mani; "Real-Time Myocardial Blood Flow Imaging in Normal Human Beings with the Use of Myocardial Contrast Echocardiography"; American Society of Echocardiography, 2001, p. 698-705.

Kinsler, Lawrence E., Frey, Austin R., Coppens, Alan B., Sanders, James V.; Fundamentals of Acoustics; John Wiley & Sons Third Edition; p. 172-174, 1982.

Gautschi, Walter; Handbook of Mathematical Functions; Dover Publications, Inc. New York; p. 295-297, 1965.

Veltmann, Christian, Lohmaier, Stefan, Schlosser, Thomas, Shai, Sonu, Ehlgen, Alexander, Pohl, Christoph, Becher, Harald, Tiemann, Klaus; "On the Design of a Capillary Flow Phantom for the Evaluation of Ultrasound Contrast Agents at Very Low Flow Velocities"; Ultrasound in Med. & Biol., vol. 28, No. 5, p. 625-634 2002.

Scabia, Marco, Biagi, Elena, Masotti, Leonardo; "Hardware and Software Platform for Real-Time Processing and Visualization of Echographic Radiofrequency Signals"; IEEE Transactions on Ultrasonics, Ferroelectrics, and Frequency Control, vol. 49, No. 10, Oct. 2002 p. 1444-1452.

Qian, Hong, Bassingthwaighte, James B.; "A Class of Flow Bifurcation Models with Lognormal Distribution and Fractal Dispersion"; J. theor. Biol. Academic Press (2000) p. 205, 261-268.

Krix, Martin, Plathow, Christian, Kiessling, Fabian, Herth, Felix, Karcher, Andreas, Essig, Marco, Schmitteckert, Harry, Kauczor, Hans-Ulrich, Delorme, Stefan; "Quantification of Perfusion of Liver Tissue and Metastases Using a Multivessel Model for Replenishment Kinetics of Ultrasound Contrast Agents"; Ultrasound in Med. & Biol., vol. 30, No. 10 p. 1355-1363, 2004.

Lucidarme, Olivier, Franchi-Abella, Stephanie, Correas, Jean-Michel, Bridal, S. Lori; Kurtisovski, Erol, Berger, Genevieve; Blood Flow Quantification with Contrast-enhanced US: "Entrance in the Section" Phenomenon-Phantom and Rabbit Study; Experimental Blood Flow Quantification: "Entrance in the Section" Phenomenon; Radiology; 2003; vol. 228 No. 2, 473-479.

Eyding, Jens, Wilkening, Wilko, Dipl-Ing, Reckhardt, Markus , Schmid, Gebhard, Meves, Saskia, Ermert, Helmut, Przuntek, Horst, Postert, Thomas; "Contrast Burst Depletion Imaging (CODIM) A New Imaging Procedure and Analysis Method for Semiquantitative Ultrasonic Perfusion Imaging"; STROKE, vol. 34, Jan. 2003 p. 77-83; XP002354455.

Cosgrove, David, Eckersly, Robert, Blomley, Martin, Harvey, Christopher; "Quantification of Blood Flow"; Eur. Radiol. (2001) vol. 11, No. 8, 2001, 1338-1344.

* cited by examiner

PERFUSION ASSESSMENT METHOD AND SYSTEM BASED ON BOLUS ADMINISTRATION

PRIORITY CLAIM

The present application is a national phase application filed pursuant to 35 USC §371 of International Patent Application Serial No. PCT/EP2005/057065, published in English, filed Dec. 21, 2005, which claims the benefit of European Patent Application No. 04106962.6, filed Dec. 23, 2004, which are incorporated by reference herein in their entireties.

CROSS REFERENCE TO RELATED APPLICATIONS

This application is related to U.S. patent application Ser. No. 11/302,415, filed Dec. 12, 2005, and U.S. patent application Ser. No. 11/823,098, filed Jun. 25, 2007, which are incorporated by reference herein in their entireties.

TECHNICAL FIELD

An embodiment of the present invention relates to the diagnostic imaging field. More specifically, an embodiment of the present invention relates to blood perfusion assessment through echo-power signal analysis of a contrast agent; particularly, an embodiment of the invention is aimed at implementing the perfusion assessment when the contrast agent is administered as a bolus.

BACKGROUND

Diagnostic imaging is an emerging technique in the field of medical equipment. For example, this technique is typically exploited for the assessment of blood perfusion, which finds use in several diagnostic applications and especially in ultrasound analysis. The perfusion assessment is based on the analysis of a sequence of ultrasound contrast images, obtainable by administering an ultrasound contrast agent (UCA) to a patient. The contrast agent acts as an efficient ultrasound reflector, so that it can be easily detected applying ultrasound waves and measuring a resulting echo-power signal. As the contrast agent flows at the same velocity as the blood in the subject, its tracking provides information about the perfusion of the blood in a body-part to be analyzed.

Suitable contrast agents include suspensions of gas bubbles in a liquid carrier. For this purpose, the gas bubbles are stabilized using emulsifiers, oils, thickeners or sugars, or by entraining or encapsulating the gas or a precursor thereof into a variety of systems. Stabilized gas bubbles are generally referred to as gas-filled microvesicles. The microvesicles include gas bubbles dispersed in an aqueous medium and bound at the gas/liquid interface by a very thin envelope involving a surfactant, i.e., an amphiphilic material (also known as microbubbles). Alternatively, the microvesicles include suspensions in which the gas bubbles are surrounded by a solid material envelope formed of natural or synthetic polymers (also known as microballoons or microcapsules). Another kind of ultrasound contrast agent includes suspensions of porous microparticles of polymers or other solids, which carry gas bubbles entrapped within the pores of the microparticles. Examples of suitable aqueous suspensions of microvesicles, in particular microbubbles and microballoons, and of the preparation thereof are described in EP-A-0458745, WO-A-91/15244, EP-A-0554213, WO-A-94/09829 and WO-A-95/16467, which are incorporated herein by reference.

The perfusion assessment process is typically implemented with the so-called destruction-replenishment technique. For this purpose, the body-part to be analyzed is first perfused with the contrast agent at a constant rate. The microbubbles are then destroyed by a flash of sufficient energy. Observation of the replenishment (or reperfusion) of the microbubbles in the body-part provides quantitative information about the local blood perfusion. For this purpose, the echo-power signal that is measured over time is fitted by a mathematical model, in order to extract quantitative indicators of blood perfusion; the information thus obtained can then be used to infer a physiological condition of the body-part. This technique has been proposed for the first time in Wei, K., Jayaweera, A. R., Firoozan, S., Linka, A., Skyba, D. M., and Kaul, S., "Quantification of Myocardial Blood Flow With Ultrasound-Induced Destruction of Microbubbles Administered as a Constant Venous Infusion," Circulation, vol. 97 1998, which is incorporated herein by reference.

The mathematical models known in the art are generally based on the assumption that the contrast agent enters the body-part under analysis with a constant concentration during the reperfusion. For this purpose, the contrast agent must be provided as a continuous infusion. However, this requires an automatic infusion pump that provides a constant supply of the contrast agent through a catheter. Moreover, the continuous administration involves the use of a large amount of contrast agent. All of the above may increase the cost of the perfusion assessment process.

A different solution known in the art is that of administering the contrast agent as a bolus (i.e., a single dose provided over a short period of time, typically of the order of 2-20 seconds). In this case, the operation of providing the contrast agent is very simple, and it can be carried out by hand (for example, using a syringe); moreover, the bolus administration requires a small amount of contrast agent.

However, an inflow of the contrast agent in the body-part is not stationary in this case. Indeed, a typical bolus-type inflow shows a wash-in phase (in which the inflow increases over time following the bolus administration) and a wash-out phase (in which the inflow decreases after reaching its maximum value); moreover, the inflow of the contrast agent is generally different in a number of regions of the body-part at the same time. Therefore, in these conditions the mathematical models known in the art are not suitable for a rigorous representation of the perfusion process.

Attempts have been made to overcome the above-mentioned problem by administering the contrast agent as a "slow" bolus, over a period of time long enough to perform the replenishment analysis under a fairly constant infusion rate of the contrast agent. Nevertheless steady state conditions are not achievable because of the presence of the wash-out phase of the bolus, so that the accuracy of the results obtained is strongly limited.

The document "Quantification of perfusion of liver tissue and metastases using a multivessel model for replenishment kinetics of ultrasound contrast agents", Martin Krix, Christian Plathow, Fabian Kiessling, Felix Herth, Andreas Karcher, Marco Essig, Harry Schmitteckert, Hans-Ulrich Kauczor, and Stefan Delorme, Ultrasound in Med. & Biol., Vol. 30, No. 10, pp. 1355-1363, 2004, which is incorporated herein by reference, proposes obtaining a whole perfusion curve by means of a further identical bolus administration. However, this requires additional operations on the patient that are time consuming. In any case, the accuracy of the results so obtained is very poor, due to the fact that it is difficult (if not impossible) to have two distinct bolus administrations that are really identical.

SUMMARY

According to an embodiment of the present invention, a mathematical model is provided for describing the reperfusion of a contrast agent following destruction when administered as a bolus.

Particularly, an embodiment of the present invention proposes a perfusion assessment system. The system includes means for providing an echo-power signal indicative of a perfusion of a contrast agent in a body-part under analysis (when the contrast agent is administered as a bolus and undergoes a significant destruction during a passage of the contrast agent in the body-part). Means is provided for associating the echo-power signal to a model function; the model function includes the product between a bolus function (indicative of the passage of the contrast agent without said destruction) and a reperfusion function (indicative of a reperfusion of the contrast agent in the body part following the destruction corresponding to a substantially constant inflow of the contrast agent). The system further includes means for estimating at least one perfusion indicator from the bolus function, the reperfusion function, or a combination thereof.

An embodiment of the proposed solution avoids the need of establishing a constant inflow of the contrast agent; therefore, the perfusion process can be implemented in a very simple manner (for example, with a syringe that is operated by hand), and with a small amount of contrast agent. All of the above strongly reduces the cost of the perfusion process.

In this way, it is possible to extract quantitative indicators of the perfusion process directly from the echo-power signal that is measured during the reperfusion of the contrast agent (administered as a bolus).

This result is achieved with a single bolus administration, without requiring any additional operation on the patient.

The different embodiments of the invention described in the following provide additional advantages.

For example, the reperfusion function has an S-shape; the S-shape includes an initial portion with substantially zero first derivatives, a final portion with substantially zero first derivatives, and a central portion (between the initial portion and the final portion) changing monotonically from a value of the initial portion to a value of the final portion.

In this way, the results are independent of the equipments used and of their settings; therefore, this information can be compared among different investigators (even if they use different equipments or settings), and it can be suitable for absolute quantitative evaluations.

For example, the echo-power signal is made proportional to a concentration of the contrast agent in the body-part (e.g., by linearization of log-compressed images).

In this way, it is possible to associate the echo-power signal to the (S-shape) reperfusion function directly (e.g., by a curve fitting process).

For example, the reperfusion function is a cumulative lognormal function.

This choice has been found beneficial for providing haemodynamic information about the body-part. Examples of haemodynamic parameters are, for instance, the blood volume, blood velocity, and blood flow rate.

In another embodiment of the invention, the reperfusion function is based on a plurality of elementary reperfusion functions with said S-shape (each one for a corresponding value of a perfusion parameter, or more), which are weighted according to a probability density distribution of the perfusion parameter; the perfusion indicator(s) then consist of shape indicator(s) of the probability density distribution.

The devised technique provides information about the morphology of the micro-vascular network of the body-part.

For example, each elementary reperfusion function is a cumulative normal distribution function (based on predetermined parameters of the equipment that has been used to acquire the echo-power signal).

In an embodiment of the invention, the probability density distribution (for example, of the transit time) is assumed to be a lognormal function. In this case, the reperfusion function (including the integral of the elementary reperfusion functions multiplied by the lognormal function) is represented by corresponding fitting parameters; the shape indicator(s) can then be calculated from those fitting parameters.

An embodiment of the proposed technique is relatively simple, but at the same time effective.

Alternatively, the probability density distribution is represented by a vector of probabilities, so that the reperfusion function includes the summation of the elementary perfusion functions multiplied by the corresponding probabilities; in this case, the shape indicator(s) can be calculated from the vector of probabilities.

This implementation allows estimating the actual nature of the probability density distribution.

As a further embodiment, the bolus function includes the sum of a plurality of elementary bolus functions.

This allows taking into account any recirculation of the contrast agent in the body-part before the completion of the perfusion assessment process.

For example, the bolus function and each elementary bolus function is a lognormal function.

An embodiment of the present invention also proposes a diagnostic imaging equipment based on the above-described system (and including ultrasound means for acquiring the echo-power signal).

A way to further improve the solution is to trigger the destruction of the contrast agent in response to the detection of a maximum of the echo-power signal.

This allows obtaining both a good estimation of the bolus function and a significant echo-power signal (for the estimation of the reperfusion function).

Another embodiment of the present invention proposes a corresponding perfusion assessment method.

A further embodiment of the present invention proposes a computer program for performing the method.

A still further embodiment of the invention proposes a product embodying the program.

BRIEF DESCRIPTION OF THE DRAWINGS

One or more embodiments of the invention itself, however, as well as features and advantages thereof, will be best understood by reference to the following detailed description, given purely by way of a non-restrictive indication, to be read in conjunction with the accompanying drawings.

DETAILED DESCRIPTION

Figure 1:
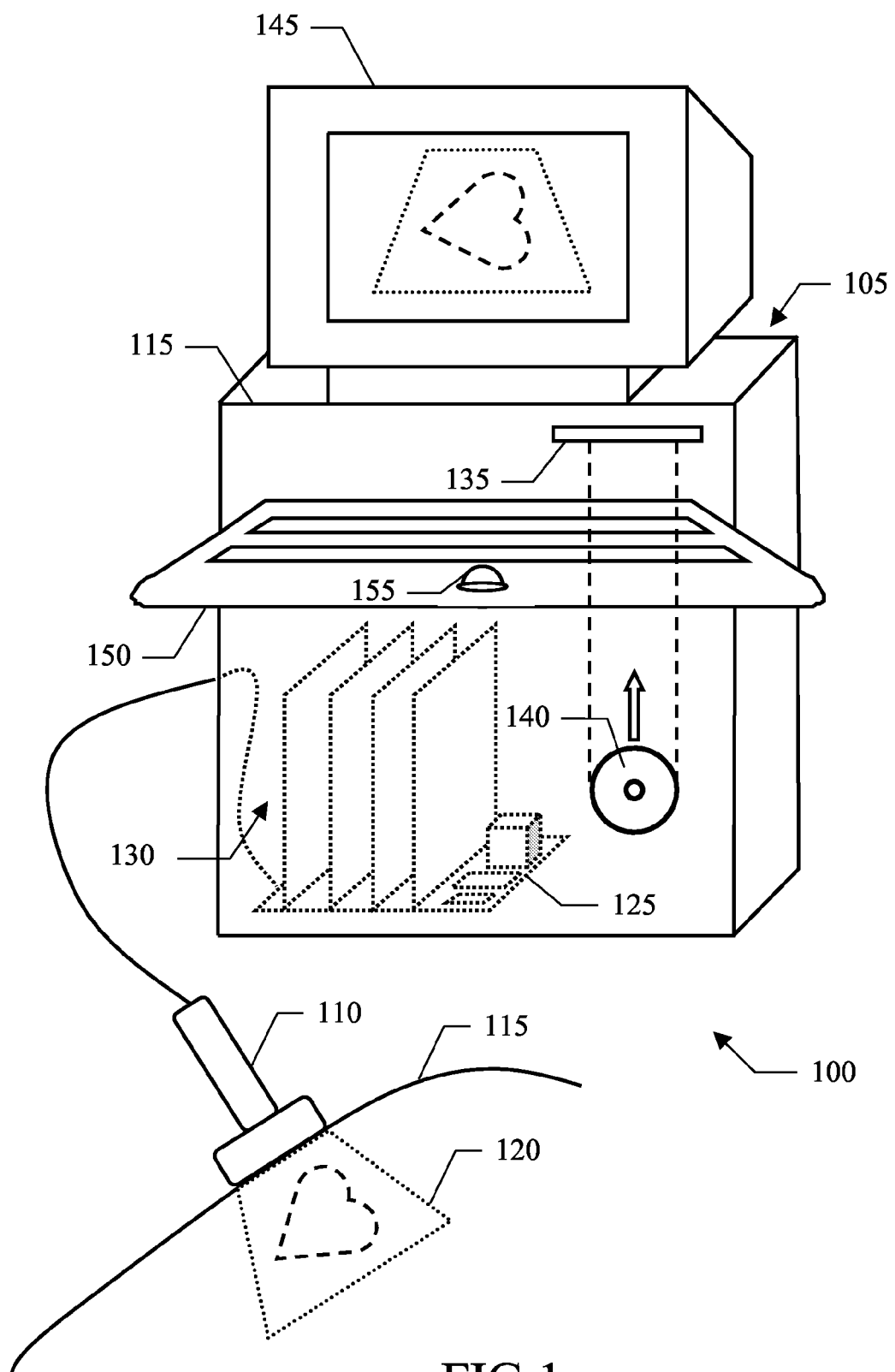
FIG. 1 is a pictorial representation of a diagnostic imaging equipment in which the solution according to an embodiment of the invention is applicable.

With reference in particular to FIG. 1, an embodiment of a diagnostic imaging equipment 100 is illustrated. Particularly, the equipment 100 consists of an ultrasound scanner having a central unit 105 with a hand-held transmit-receive array probe 110 (of the linear or matrix type). The probe 110 transmits ultrasound pulses (for example, having a center frequency between 2 and 10 MHz), and receives echo-power signals resulting from the reflection of the ultrasound pulses (when in contact with the skin of a patient 115 in the area of a body-part 120 to be analyzed); for this purpose, the probe 110 is provided with a transmit/receive multiplexer, which allows using the probe 110 in the above-mentioned pulse-echo mode.

The central unit 105 houses a motherboard 125, on which the electronic circuits controlling operation of the scanner 100 (such as a microprocessor, a working memory and a hard-disk drive) are mounted. Moreover, one or more daughter boards (denoted as a whole with 130) are plugged on the motherboard 125; the daughter boards 130 provide the electronic circuits for driving the probe 110 and processing its signals. The scanner 100 can also be equipped with a drive 135 for reading removable disks 140 (such as floppy-disks). A monitor 145 is used to display an image representing the body-part 120 under analysis. Moreover, a keyboard 150 is connected to the central unit 105 in a conventional manner; the keyboard 150 is provided with a trackball 155, which is used to manipulate the position of a pointer (not shown in the figure) on a screen of the monitor 145.

The ultrasound scanner 100 is used to assess blood perfusion in the body-part 120. For this purpose, a contrast agent is administered to the patient 115; the contrast agent may be provided either with a continuous administration (by means of a suitable pump) or as a bolus (typically by hand with a syringe). After a predetermined period (for example, a few seconds) ensuring that the contrast agent has filled the body-part 120, one of more ultrasound pulses with high acoustic energy (flash) are applied; the acoustic energy must be sufficient (such as with a mechanical index of 1-2) to cause the destruction of a significant portion of the microbubbles (for example, at least 50%); this allows the detection of a substantial variation of the received echo-power signal between the value measured right after the application of the destruction pulses and when the body-part is replenished by the contrast agent. A series of ultrasound pulses with low acoustic energy (such as with a mechanical index of 0.01-0.1) is then applied, so as to involve no further destruction of the contrast agent; resulting ultrasound images are recorded continuously (for example, at time intervals of 30-80 ms), in order to track the reperfusion flow of the contrast agent into the body-part 120.

Figure 2A:
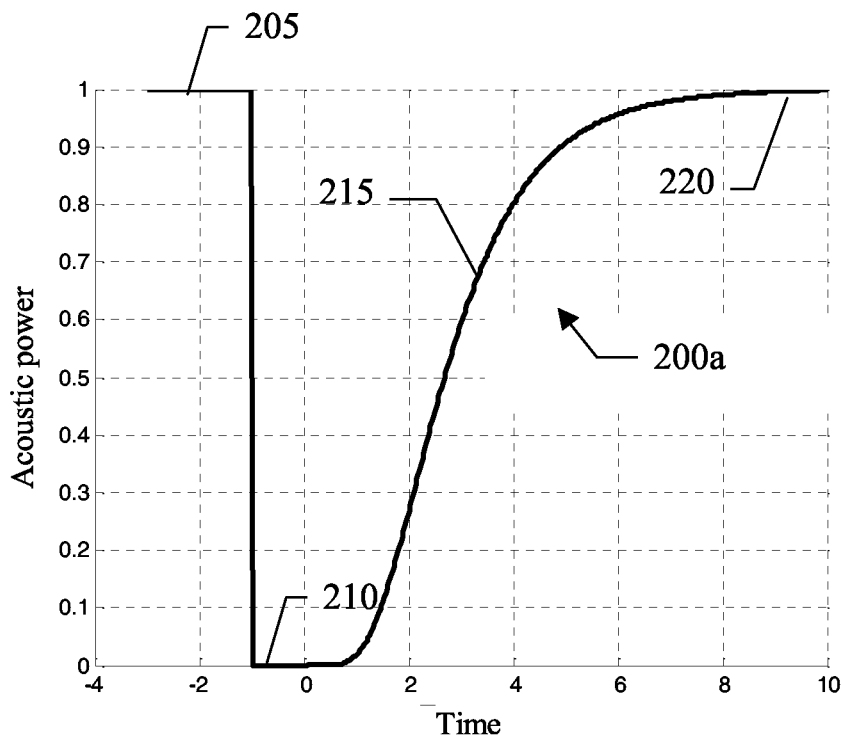
FIG. 2a shows an exemplary evolution of an echo-power signal over time in a perfusion process based on a continuous administration of a contrast agent with destruction frames applied over a one-second interval.

Moving now to FIG. 2a, when the contrast agent is provided as a continuous administration, the evolution over time of the echo-power signal during the reperfusion of the body-part can be schematically represented by a curve 200a (in terms of an arbitrary unit, or a.u.). As can be seen, the reperfusion curve 200a initially has a steady value (in a portion 205), due to the constant inflow of the contrast agent. The application of the destruction pulses result in a momentary increase of the echo-power signal (not shown), which is irrelevant for the analysis and thus assigned a value of zero; immediately after the destruction pulses have been applied, the value of the echo-power signal is substantially zero (portion 210). The contrast agent then replenishes the body-part, so that the echo-power signal gradually increases (portion 215) towards its asymptotic value equal to the one before the application of the destruction pulses (portion 220).

Figure 2B:
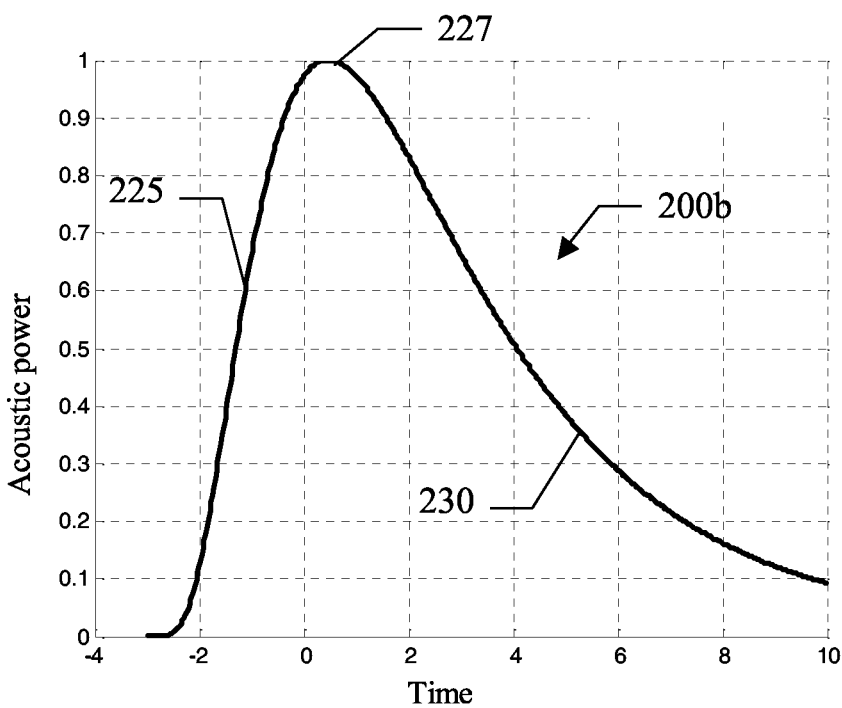
FIG. 2b shows an exemplary evolution of the echo-power signal over time during a bolus administration (without any destruction of the contrast agent)

On the other hand, as shown in FIG. 2b, the evolution over time of the echo-power signal during a bolus administration (without any destruction of the contrast agent) can be schematically represented by a curve 200b. The bolus curve 200b has an initial portion 225, wherein the echo-power signal increases (during a wash-in phase following the administration of the contrast agent) towards a rounded peak 227. Once the echo-power signal has reached its maximum value, it starts decreasing as a result of a wash-out phase of the contrast agent (portion 230).

Figure 2C:
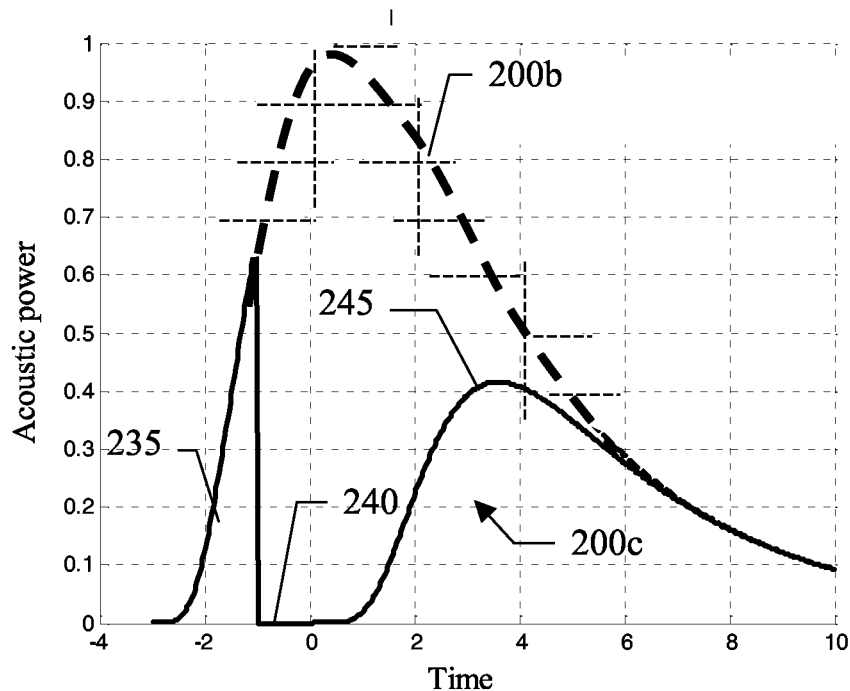
FIG. 2c shows an exemplary evolution of an echo-power signal over time in a perfusion process based on the bolus administration and destruction of the contrast agent.

Considering now FIG. 2c, the evolution over time of the echo-power signal for a contrast agent administered as a bolus but subjected to the destruction pulses can be schematically represented with a curve 200c (in solid line). In this case, the bolus-reperfusion curve 200c has an initial portion 235 corresponding to the bolus curve 200b (in dashed line). Also in this case, the application of the destruction pulses result in a momentary increase of the echo-power signal (not shown), which is irrelevant for the analysis, and thus assigned a value of zero; immediately after the destruction pulses have been applied, the value of the echo-power signal is substantially zero (portion 240). Assuming that a sufficient amount of contrast agent remains in the blood vessels feeding the body-part, the bolus-reperfusion curve 200c then includes a portion 245 wherein the echo-power signal increases towards a rounded peak as the contrast agent replenishes the body-part, before decreasing again as a result of its wash-out phase (moving asymptotically towards the bolus curve 200b).

Figure 2D:
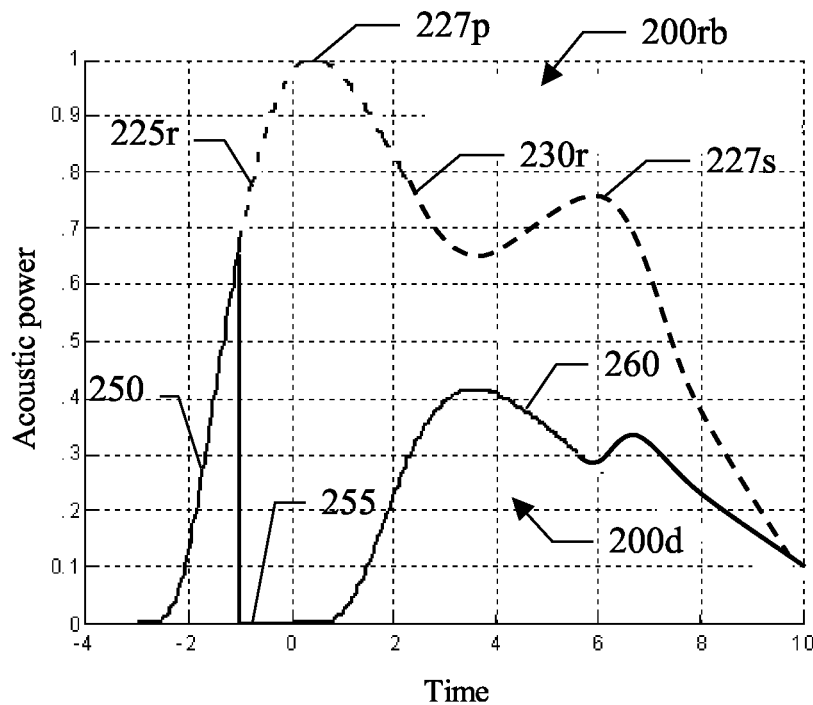
FIG. 2d shows an exemplary evolution of an echo-power signal over time in a perfusion process based on the bolus administration with recirculation of the contrast agent.

A more complex situation arises when the contrast agent recirculates in the body-part before the completion of the wash-out phase of the bolus. Indeed, the contrast agent administered to the patient follows its normal cycle of circulation of the blood, so that it passes again in the body-part under analysis after each blood cycle. However, the microbubbles gradually dilute in the blood, so that the inflow of the contrast agent in the body-part decreases at every blood circulation cycle (substantially disappearing, for example, after one or two blood circulation cycles). In this case, as shown in FIG. 2d, the evolution over time of the echo-power signal during a bolus administration with recirculation (without any destruction of the contrast agent) can be schematically represented by a curve 200rb (in dashed line). This recirculation bolus curve 200rb is similar to the bolus curve described above, with a (primary) peak 227p at the end of a portion 225r (corresponding to the wash-in phase); however, a secondary rounded peak 227s (with an intensity lower than the one of the primary peak 227p) is now present in a portion 230r (corresponding to the wash-out phase); the secondary peak 227s is caused by the transient increase of the echo-power signal, due to the recirculation of the contrast agent. Similar considerations apply if one or more additional secondary peaks (with decreasing intensity) are caused by any further recirculation of the contrast agent in the body-part.

Therefore, the evolution over time of the echo-power signal for a contrast agent administered as a bolus with recirculation but subjected to the destruction pulses can be schematically represented with a curve 200d (in solid line). Also in this case, the recirculation bolus-reperfusion curve 200d has an initial portion 250 corresponding to the recirculation bolus curve 200rb, and a portion 255 at the value zero ("ignored" part of the image sequence corresponding to the application of the destruction pulses). The recirculation bolus-reperfusion curve 200d then includes a portion 260, wherein the echo-power signal increases towards a rounded peak as the contrast agent replenishes the body-part before decreasing again as a result of its wash-out phase (moving asymptotically towards the recirculation bolus-reperfusion curve 200rb), with a further rounded peak of lower intensity due to the recirculation of the contrast agent.

In any case, it has been observed that the evolution of the echo-power signal during the perfusion process when the contrast agent is administered as a bolus (with or without any recirculation) can be represented mathematically with a model resulting from the combination of one model relating to the bolus administration and another model relating to a reperfusion process with a constant inflow of the contrast agent.

Considering in particular the bolus administration (without any recirculation), a realistic model for a bolus function B(t) (representing an acoustic power that is measured by the probe over time) is a lognormal function (i.e., a normal distribution function of the natural logarithm of an independent variable):

$$B(t) = A \cdot \frac{e^{-\frac{[\ln(t-t_0)-m_B]^2}{2s_B^2}}}{(t-t_o) \cdot s_B \sqrt{2\pi}},$$

where the value $t_0$ represents an arbitrary time interval between the instant of the bolus administration and the choice of a time origin for the analysis (with the bolus function B(t) that is defined for $t > t_0$), and A is an amplitude parameter (which can be interpreted as the blood volume in the body-part); in addition, the parameters $m_B$ and $s_B$ are the mean and standard deviation of the distribution of the natural logarithm of $(t-t_0)$, respectively.

Figure 3:
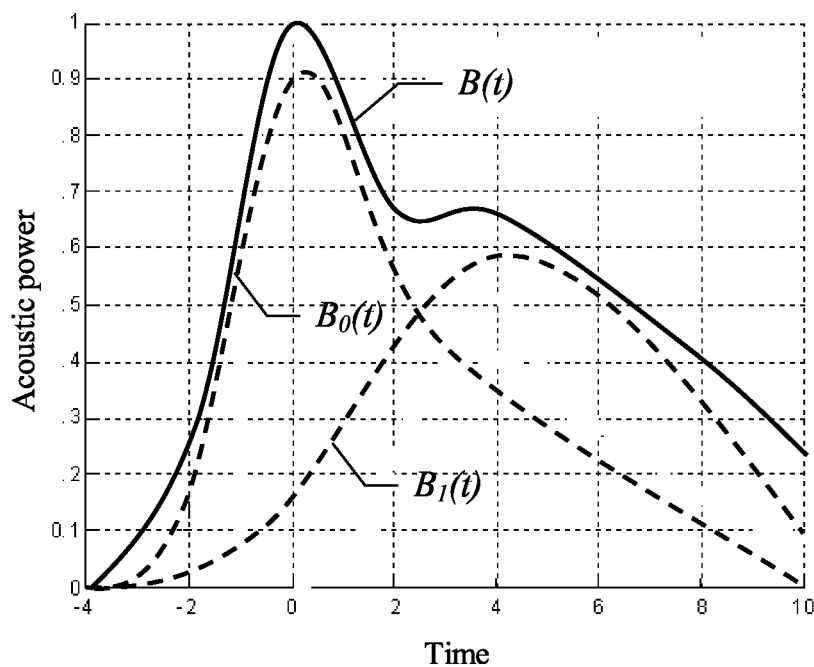
FIG. 3 illustrates a bolus function according to an embodiment of the invention.

On the other hand, as shown in FIG. 3, when the contrast agent recirculates in the body-part, the bolus function B(t) can be expressed as a combination of successive bolus passages. In this case, the first passage of the contrast agent in the body-part is represented with a (primary) elementary bolus function $B_0(t)$ with the above-described shape. Likewise, the next passage of the contrast agent can be represented with a similar (secondary) elementary bolus function $B_1(t)$; the secondary bolus function $B_1(t)$ is shifted in time (according to the delay of the recirculation) and exhibits a lower intensity (due to the dilution of the contrast agent). Similar considerations apply to any further recirculation. Therefore, the bolus function B(t) can be mathematically expressed as the sum of the elementary bolus functions $B_h(t)$ (with h=0 ... R, where R represents the number of recirculations to be taken into account, for example, 2-4):

$$B(t) = \sum_{h=0}^{R} B_h(t) = \sum_{h=0}^{R} A \cdot \frac{e^{-\frac{[\ln(t-t_{oh})-m_{Bh}]^2}{2s_{Bh}^2}}}{(t-t_{oh}) \cdot s_{Bh} \sqrt{2\pi}}.$$

As in the case described above, the parameters $m_{Bh}$ and $s_{Bh}$ are the mean and standard deviation of the distribution of the natural logarithms of t, respectively, of the $h^{th}$ lognormal function (based on a corresponding time interval $t_{oh}$).

With reference instead to the reperfusion process corresponding to the constant inflow of the contrast agent, a reperfusion function I(t) representing the video gray level that is measured over time during the process is generally represented with a mono-exponential function:

$$I(t) = A \cdot (1 - e^{-\beta \cdot t}),$$

where A is the steady-state amplitude, $\beta$ is a "velocity" term of the mono-exponential function, and the time origin is taken at the instant immediately following the last destruction pulses. In the prior art (e.g., the cited articles by Wei et al.), the values A, $\beta$ and A$\beta$ have commonly been interpreted as quantities proportional to "blood volume", "blood velocity" and "blood flow" within the body-part under analysis.

However, in an embodiment of the invention the reperfusion function E(t) is instead expressed with a different function having an S-shape. The S-shape function includes an initial and a final flat portion (or plateau) with a substantially constant initial value and final value, respectively; in a central portion between the initial portion and the final portion, the S-shape function changes monotonically from the initial value to the final value. In other words, the S-shape function has essentially zero first derivatives in its initial and final portions; moreover, the S-shape function preferably has one or more zero second derivatives in its central portion.

Figure 4A:
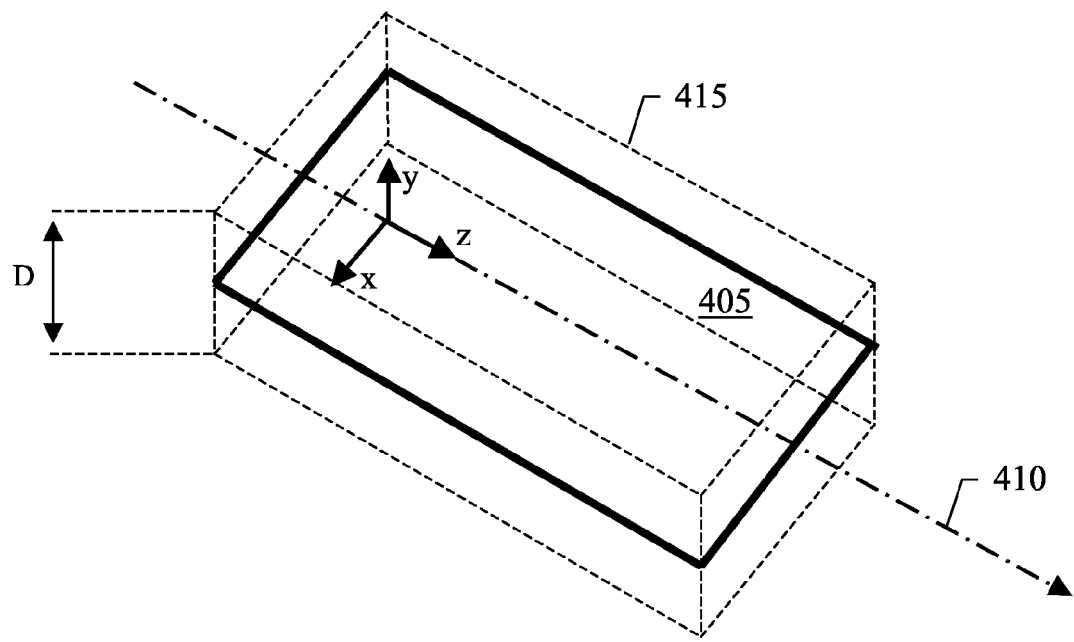
FIG. 4a is a schematic representation of an imaging plane of the diagnostic imaging equipment.

In order to explain the theoretical reasons of this choice, it should be considered that the reperfusion process, as shown in FIG. 4a, is based on a tomographic approach wherein an imaging plane 405 is rapidly scanned by an ultrasound beam propagating along a direction 410. A coordinate system can then be defined with an axis x orthogonal to the propagation direction 410 in the imaging plane 405 (lateral direction), an axis y orthogonal to the imaging plane 405 (elevation direction), and an axis z along the propagation direction 410 (depth direction). The microbubbles are destroyed in a slice 415, which extends symmetrically on either side of the imaging plane 405. The slice 415 has an extension determined by the area scanned by the ultrasound beam, and a thickness D determined by its pressure distribution in the elevation direction y.

The echo-power signal that is measured during the replenishment of the slice 415 by the microbubbles is governed, on the one hand, by the local flow rate of the blood (defining the unknown perfusion parameters to be estimated), and, on the other hand, by the acoustic sensitivity pattern of the probe in essentially the elevation direction y. The acoustic sensitivity pattern can be determined according to the combined effects of its spatial distribution in the transmit mode and in the receive mode (which may be different in general).

Particularly, in the transmit mode an acoustic pressure distribution pa(y) in the elevation direction y (assuming a focusing aperture of the probe with rectangular geometry) is approximately given by the function:

$$p_{Tx}(y) \cong \Gamma \cdot \sin c(K_{Tx}y),$$

where $\Gamma$ is an arbitrary proportionality constant and the function sin c(u), for a generic variable u, stands for $$\sin c(u) = \frac{\sin(\pi u)}{\pi u};$$

moreover, $$K_{Tx} = \frac{2a}{\lambda z},$$

with a the probe half-aperture in the elevation direction, $\lambda$ the ultrasound wavelength ( $$\lambda = \frac{c}{f},$$

with c the speed of sound in the body-part and f the ultrasound frequency), and z the distance from the probe along the depth direction. The above-described function applies to an excitation in the continuous wave mode; in the case of an excitation in the pulsed mode, as is generally the case in the ultrasound scanners, the main lobe of the peak-pressure distribution is in close agreement with the continuous wave case at a frequency near the center (or mean) frequency of the acoustic pulsed waveform.

A corresponding acoustic power distribution $P_{Tx}(y)$ is approximately determined by the square of the pressure distribution pa(y), that is:

$$P_{Tx}(y) \cong p_{Tx}^2(y) \cong \sin c^2(K_{Tx}y).$$

In practice, the acoustic power distribution $P_{Tx}(y)$ can be approximated by a normal (or Gaussian) function according to:

$$P_{Tx}(y) \cong e^{-(1.94 \cdot K_{Tx} \cdot y)^2}.$$

In the receive mode, a similar approximation of the acoustic power distribution $P_{Rx}(y)$ provides:

$$P_{Rx}(y) \cong e^{-(1.94 \cdot K_{Rx} \cdot y)^2},$$

where the parameter $K_{Rx}$ is determined as indicated above but according to the receive conditions.

An acoustic power sensitivity distribution PE(y) of the probe in the y direction is, in a first approximation, determined by the product of the acoustic power distribution in the transmit mode $P_{Tx}(y)$ and the acoustic power distribution in the receive mode $P_{Rx}(y)$; therefore, the power sensitivity distribution PE(y) can be defined by a normal function as:

$$PE(y) = P_{Tx}(y) \cdot P_{Rx}(y) \cong e^{-(1.94 \cdot K_{Tx} \cdot y)^2} \cdot e^{-(1.94 \cdot K_{Rx} \cdot y)^2} = e^{-(1.94 \cdot y)^2 \cdot (K_{Tx}^2 + K_{Rx}^2)} = e^{-(1.94 \cdot K \cdot y)^2},$$

where the parameter $K^2 = K_{Tx}^2 + K_{Rx}^2$ is determined according to the transmit-receive conditions. This function can also be expressed for values of the unitless quantity $Y = K \cdot y$ as:

$$PE(Y) \cong e^{-(1.94 \cdot Y)^2}.$$

Practically, the value K may be determined theoretically as discussed above; alternatively, the value K may be determined experimentally by scanning a small reflector across the imaging plane 405, in the elevation direction y, and then best fitting the recorded echo-power signal to the above-described function.

Figure 4B:
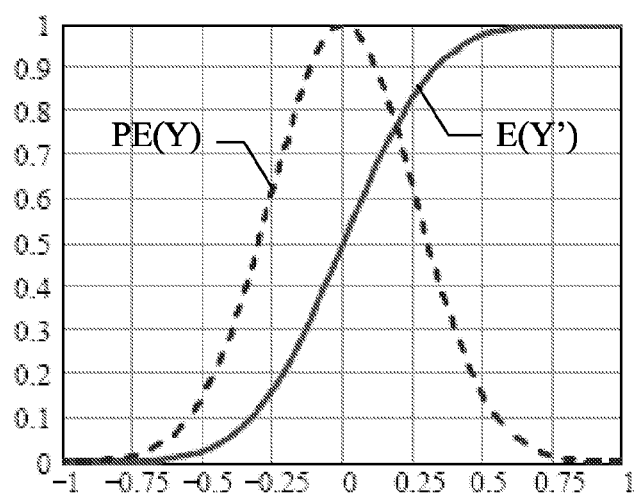
FIG. 4b is a graph showing an exemplary acoustic power distribution of the equipment and its corresponding integral.

As illustrated in FIG. 4b, the acoustic power distribution PE(Y) takes its maximum value 1 for Y=0. An acoustic power E(Y') of the echo-power signal that is measured by the probe when the microbubbles have replenished the slice 215 until a position y'=Y'/K can then be expressed as the integral of the acoustic power sensitivity distribution PE(Y) for the value Y', that is:

$$E(Y') = \int_{-\infty}^{Y'} PE(Y) dY.$$

As can be seen in the figure, the integral of the acoustic power distribution PE(Y') is represented by a function with an S-shape. Particularly, in the example at issue the S-shape function has the constant value 0 in its initial portion and the constant value 1 in its final portion; in the central portion, between the initial portion and the final portion, the S-shape function changes monotonically from the initial value to the final value (with the half-amplitude value 0.5 that is reached when Y'=0).

For example, the S-shape function defined by the integral of the acoustic power distribution PE(Y') can be represented by a cumulative normal distribution function (referred to as perf function in this context), as a function of an arbitrary variable q:

$$perf(q) = \frac{1}{\sqrt{\pi}} \int_{-\infty}^{q} e^{-u^2} du.$$

Furthermore, the perf function can be simply expressed in terms of an error function erf(q) as:

$$perf(q) = 0.5 \cdot [1 + erf(q)],$$

where:

$$erf(q) = \frac{2}{\sqrt{\pi}} \int_{0}^{q} e^{-u^2} du.$$

Figure 5:
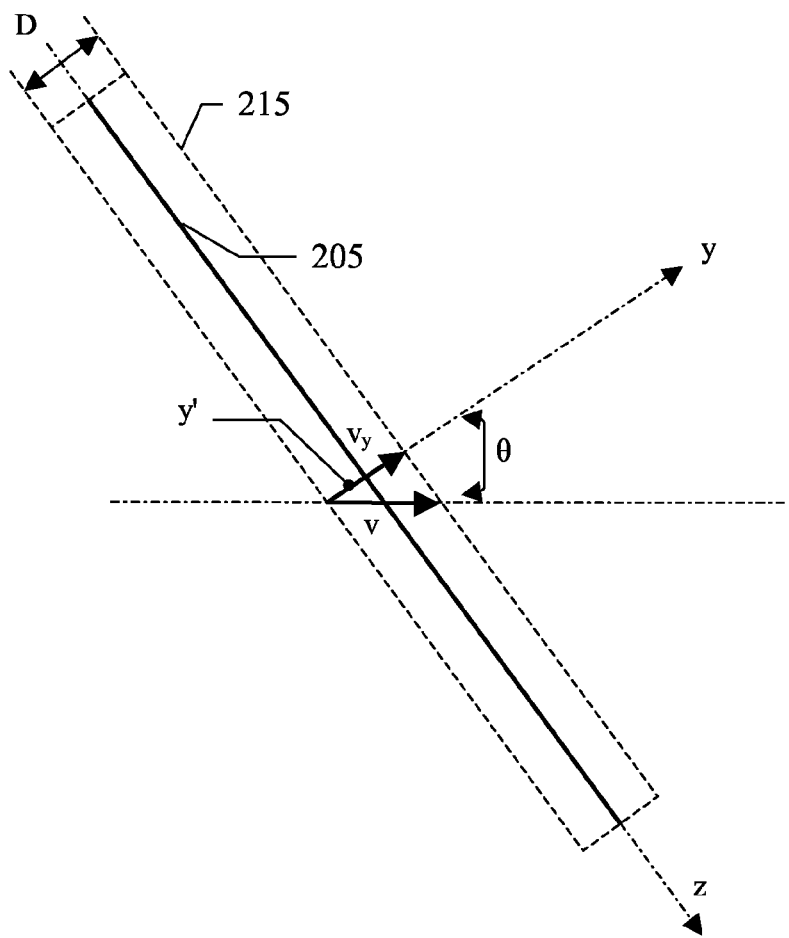
FIG. 5 is a schematic representation of the analysis of a typical perfusion process.

During the reperfusion process, as shown in FIG. 5, the microbubbles replenish the slice 415 with a velocity v; the component of the velocity v along the elevation direction y is then:

$$v_y = v \cdot \cos(\theta),$$

where $\theta$ is the angle between the velocity v and the elevation direction y. The location of the microbubbles in the replenishment slice 415 can then be expressed as a function of time as:

$$y' = v_y \cdot (t - \tau),$$

where $$\tau = \frac{D}{2v_y}$$

represents the transit time of the microbubbles in the slice 415, defined as the time delay required for them to travel from the edge of the slice 415 to its central portion (corresponding to the image plane 405). Therefore, the acoustic power that is measured over time during the reperfusion process can be expressed by the following reperfusion function E(t):

$$E(t) = O + A \cdot perf(q)$$
$$= O + A \cdot perf(1.94 \cdot Y')$$
$$= O + A \cdot perf(1.94 \cdot K \cdot y') =$$
$$= O + A \cdot perf[1.94 \cdot K v_y(t-\tau)],$$

where O and A are an offset parameter and an amplitude parameter, respectively. The reperfusion function E(t) can also be expressed in terms of the transit time $\tau$ (by replacing $v_3$, with $D/2\tau$):

$$E(t) = O + A \cdot perf\left[1.94 \cdot \frac{KD}{2\tau}(t-\tau)\right],$$

or in terms of the velocity $v_y$ (by replacing $\tau$ with $D/2v_y$):

$$E(t) = O + A \cdot perf\left[1.94 \cdot \frac{K}{2} \cdot (2v_y \cdot t - D)\right].$$

Practically, the value of the thickness D may be tabulated as a function of depth in a reasonable approximation for each ultrasound scanner. Preferably, the thickness D is determined experimentally at different depths. For example, this result can be achieved by embedding microbubbles in a gel and then estimating the extent of destroyed microbubbles by direct optical observation. Alternatively, it is possible to use another ultrasound scanner (at low acoustic power) with its imaging plane perpendicular to the imaging plane of the ultrasound scanner at issue, so as to determine the extent of destroyed microbubbles acoustically (in vivo or in vitro). The thickness D may also be estimated theoretically, on the basis of the transmit beam profile and a knowledge of the threshold in acoustic pressure for microbubbles destruction; a correction factor on the values of the thickness D with depth is then applied by taking into account tissue attenuation.

In actual practice, the microbubbles replenish the slice 415 along multiple directions and with diverse velocities; in this case, the reperfusion function E(t) is obtained by combining the different contributions. Particularly, when the microbubbles flow at N velocities $v_{yi}$ (with i=0 ... N) along corresponding directions $\theta_i$ (and then with transit times $$\tau_i = \frac{D}{2v_{yi}}$$

) the reperfusion function E(t) can be expressed in the continuous form as:

$$E(t) = O + A \cdot \int_0^\infty C(\tau) \cdot perf\left[1.94 \cdot \frac{KD}{2\tau}(t-\tau)\right] \cdot d\tau$$

or $$E(t) = O + A \cdot \int_0^\infty C(\tau) \cdot perf\left[1.94 \cdot \frac{K}{2} \cdot (2v_y \cdot t - D)\right] \cdot dv_y,$$

where the function $C(\tau)$ represents a relative concentration of the microbubbles. Likewise, the reperfusion function E(t) can also be expressed in the discrete form as:

$$E(t) = O + A \cdot \sum_{i=0}^{N} C_i \cdot perf\left[1.94 \cdot \frac{KD}{2\tau_i}(t-\tau_i)\right] \cdot (\tau_{i+1} - \tau_i)$$

or $$E(t) = O + A \cdot \sum_{i=0}^{N} C_i \cdot perf\left[1.94 \cdot \frac{K}{2} \cdot (2v_{yi} \cdot t - D)\right] \cdot (v_{yi+1} - v_{yi}),$$

where $C_i$ is the relative concentration of the microbubbles having the transit time $\tau_i$ or the velocity $v_{yi}$. The relative concentration function $C(\tau)$ and the vector of the relative concentrations $C=[V_0, \ldots, C_N]$ represent the probability density distribution of the corresponding transit times or velocities (with $0 \leq C(\tau) \leq 1$ and $$\int_0^\infty C(\tau)d\tau = 1,$$

or $0 \leq Ci \leq 1$ and $$\sum_{i=0}^{N} Ci \cdot (\tau_{i+1} - \tau_i) = 1).$$

The reperfusion function E(t) is still graphically represented by an S-shape function. In such case, the reperfusion function E(t) can be expressed in terms of a mean transit time or a mean velocity (for the sake of simplicity generically denoted with r and v, respectively). For this purpose, it has been found beneficial to use a cumulative lognormal function (referred to as logperf function in this context); when the reperfusion function E(t) is expressed in terms of the transit time $\tau$ (similar considerations apply to the velocity v), we have $$E(t) = O + \frac{A}{2} \cdot \left[1 + erf\left(\frac{\ln(t) - m}{s\sqrt{2}}\right)\right],$$

where m and s are the mean value and the standard deviation of the natural logarithms of the transit time $\tau$, respectively.

Figure 6A:
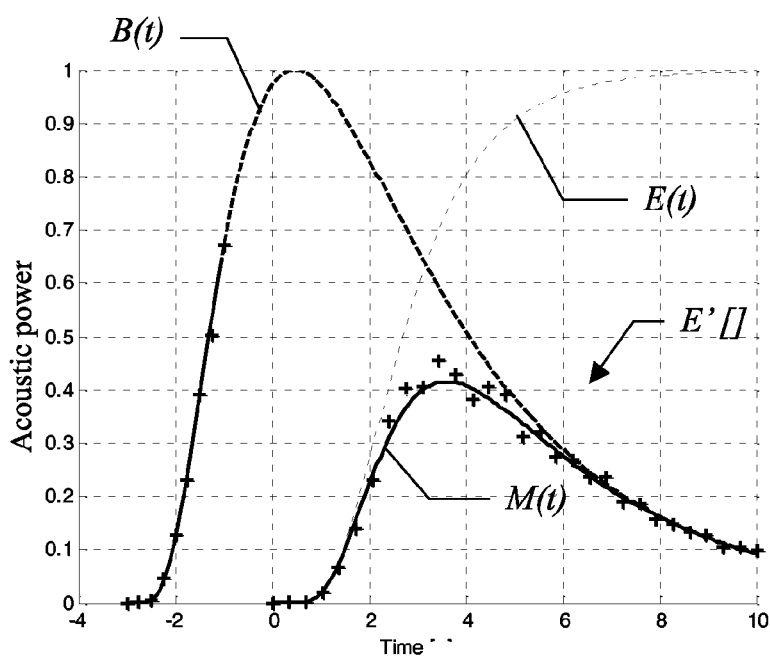
FIG. 6a shows the fitting of experimental data by a model function according to an embodiment of the invention.

Therefore, as shown in FIG. 6a, a model function M(t) representing the acoustic power that is measured over time during the actual reperfusion process of the contrast agent (when destruction pulses are applied after administering the contrast agent as a bolus) can be expressed as the product of the above-described bolus function B(t) and reperfusion function E(t). The model function M(t) is then estimated from the acoustic power that is measured over time; this result is achieved by fitting a vector of samples $E'=[E'(t_0), \ldots E'(t_M)]$ of the acoustic power at different times $t_j$ (with j=0 ... M) by the model function M(t); preferably, this operation is performed by ignoring the samples that have been measured during the application of the destruction pulses. Different quantitative indicators of blood perfusion can then be extracted from the model function M(t) thus obtained.

Particularly, whenever haemodynamic parameters of the body-part under analysis are required, the model function M(t) is expressed in terms of the reperfusion function E(t) represented by the logperf function. Assuming for the sake of simplicity that the bolus function B(t) consists of a single lognormal function (similar considerations apply if the effects of the recirculation of the contrast agent in the body-part are to be taken into account), the model function M(t) in terms of the transit time τ will be:

$$M(t) = 0 \quad \text{for } t \leq t_0$$

$$M(t) = O + A \cdot \frac{e^{-\frac{[\ln(t-t_0)-m_B]^2}{2s_B^2}}}{(t-t_o) \cdot s_B \sqrt{2\pi}} \quad \text{for } t_0 < t < t_{flash},$$

$$M(t) = O + \frac{A}{2} \cdot \frac{e^{-\frac{[\ln(t-t_0)-m_B]^2}{2s_B^2}}}{(t-t_o) \cdot s_B \sqrt{2\pi}} \cdot \left[1 + \mathrm{erf}\left(\frac{\ln(t)-m}{s\sqrt{2}}\right)\right], \quad \text{for } t > 0$$

where $t_{flash}$ represents the starting time of the destruction pulses, assumed to end at the time origin t=0. The sample vector E'[ ] is then fitted by the resulting model function M(t), so as to estimate the parameters O, A, $m_B$, $s_B$, m and s. This result can be achieved using the Trust region method described in Byrd, R. H., R. B. Schnabel, and G. A. Shultz, "Approximate Solution of the Trust Region Problem by Minimization over Two-Dimensional Subspaces", Mathematical Programming, Vol. 40, pp 247-263, 1988 (for example, implemented by the Curve fitting Toolbox of the Matlab® programming language).

The value of the fitting parameter A provides a good relative estimate of the blood volume in the slice, and the values of the fitting parameters m and s allow determining a good estimate of the mean transit time of the microbubbles ($\tau_{mean}$); in this way, it is also possible to calculate a mean flow rate of the microbubbles as $\phi_{mean} = a/\tau_{mean}$. Similar considerations apply when the mean velocity ($v_{ymean}$) is estimated.

The (haemodynamic) parameters estimated from the analysis of the logperf function exhibit a high linearity with respect to their actual values. Moreover, in sharp contrast to the prior art (i.e., the mono-exponential function), the fitting parameters so obtained are independent of the ultrasound scanner that has been used; in addition, the fitting parameters can now be related to physical quantities.

Besides, it is also possible to obtain information about the morphology of the vascularity of the body-part under analysis by estimating the probability density distribution of the transit times τ. This information is provided by the probability density function C(τ) (when the reperfusion function E(t) is in the continuous form) or by its corresponding discrete probability vector C[ ] (when the reperfusion function E(t) is in the discrete form). For this purpose, the model function M(t) is now expressed in terms of the corresponding reperfusion function E(t) (including the integral or the summation of multiple perf functions weighted by the probability density function C(τ) or the discrete probability vector C[ ], respectively).

Particularly, in a first embodiment of the invention (relating to the continuous form of the reperfusion function E(t)) the probability function C(τ) is assumed to have a lognormal distribution, which is the commonly accepted model:

$$C(\tau) = \frac{e^{-\frac{[\ln(\tau)-m]^2}{2s^2}}}{\tau \cdot s \sqrt{2\pi}},$$

where m and s are the mean and standard deviation of the distribution of the natural logarithms of τ, respectively. The sample vector E'[ ] is then fitted by the resulting model function M(t) (for t>$t_0$):

$$M(t) =$$

$$O + A \cdot \frac{e^{-\frac{[\ln(t-t_0)-m_B]^2}{2s_B^2}}}{(t-t_o) \cdot s_B \sqrt{2\pi}} \cdot \int_0^\infty \frac{e^{-\frac{[\ln(\tau)-m]^2}{2s^2}}}{\tau \cdot s \sqrt{2\pi}} \cdot \mathrm{perf}\left[1.94 \cdot \frac{KD}{2\tau}(t-\tau)\right] \cdot d\tau,$$

so as to estimate the fitting parameters O, A, $m_B$, $s_B$, m and s. Also in this case, the value of the amplitude parameter A can be related to the relative regional blood volume in the body-part under analysis. However, it is now possible to calculate any desired statistics indicator of the probability density function C(τ), such as its mean value, variance and skewness:

$$\tau_{mean} = e^{m+\frac{s^2}{2}}$$

$$\sigma^2 = e^{s^2+2m} \cdot (e^{s^2} - 1)$$

$$\gamma = \sqrt{e^{s^2} - 1} \cdot (2 + e^{s^2}).$$

Some indicators provide information about the shape of the probability density function C(τ). For example, the variance $\sigma^2$ measures the spread of the probability function C(τ), whereas the skewness γ measures its asymmetry. Particularly, the most significant shape indicator is the skewness γ, since it consists of a pure number independent of the actual values being measured.

Figure 6B:
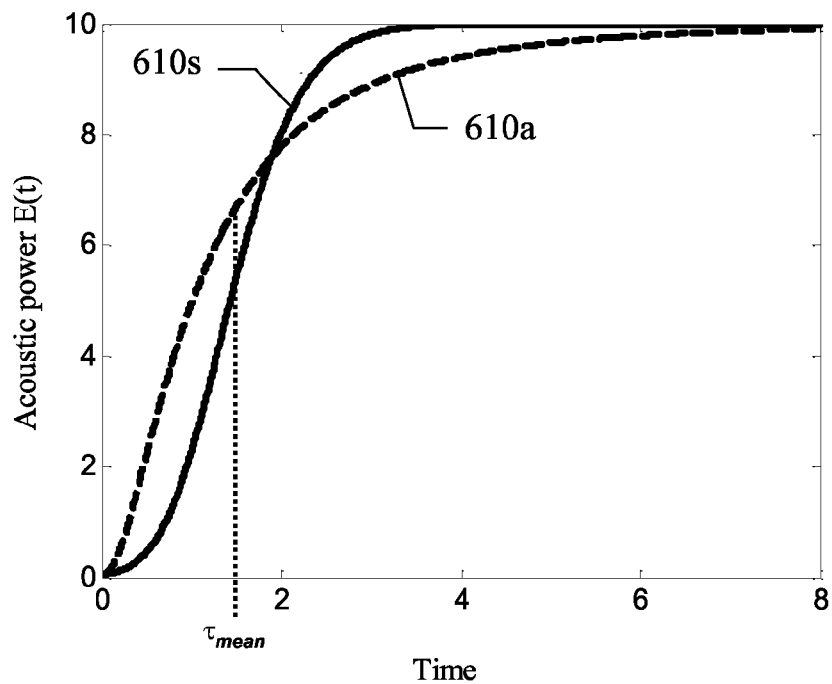
FIGS. 6b and 6c show different examples of reperfusion functions with corresponding probability density distributions.

The shape indicators so obtained can be used to characterize the morphology of the vascularity of the body-part under analysis (irrespectively of its haemodynamic parameters). For example, as shown in FIG. 6b, two different reperfusion functions E(t) (in terms of an arbitrary unit, or a.u.) are denoted with 610s and 610a. Even though both reperfusion functions 610s and 610a have the same mean transit time ($\tau_{mean}$=1.48) and the same value of the parameter A they are very different in shape. Particularly, the reperfusion function 610s is close to the perf function, with a high level of symmetry around its half-amplitude value (5 in the example at issue); conversely, the reperfusion function 610a has a distorted shape (with an initial sharper rise and a final softer shoulder), which is clearly asymmetric around the half-amplitude value.

Figure 6C:
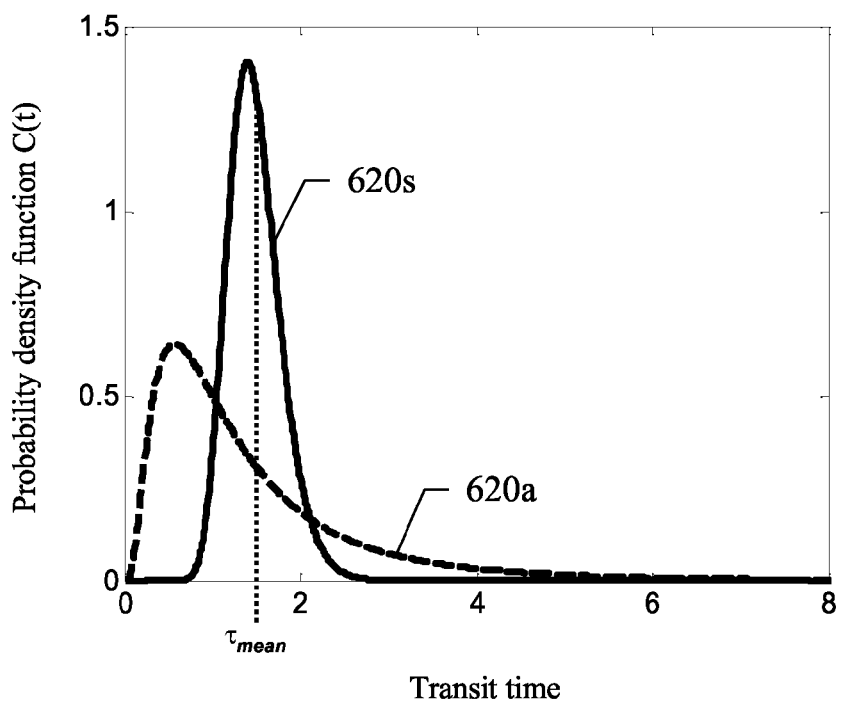

Moving to FIG. 6c, the above-described (symmetric and asymmetric) reperfusion functions are instead associated with quite different probability density functions C(τ). Particularly, the symmetric reperfusion function provides a probability density function 620s that is very close to a normal probability density function, being narrow and almost symmetric; this shape is characterized by low values of its variance and skewness ($\sigma^2$=0.09 and γ=0.61 in the example at issue). Conversely, the asymmetric reperfusion function corresponds to a probability density function 620a that is wide and asymmetric; this shape is characterized by high values of its variance and skewness ($\sigma^2$=1.97 and γ=3.69 in the example at issue).

In this way, it is possible to identify pathological conditions of the body-part under analysis. For example, a nearly symmetric probability density function $C(\tau)$ (with a low skewness $\gamma$) could be associated to healthy tissues (with a very ordered microvascular network); conversely, an asymmetric probability density function $C(\tau)$ (with a high skewness $\gamma$) could be associated to pathological tissues (with a disordered microvascular network). For example, the high skewness $\gamma$ can be indicative of an angiogenic process (i.e., a vascularization of the tissue involving the development of new blood vessels) in cancer or ischemia in coronary artery disease.

Moreover, it is also possible to monitor the evolution of a pathological condition or the response to a treatment by successive measurements of the shape indicators (and especially the skewness $\gamma$) over time. Indeed, any changes in the skewness $\gamma$ denote a corresponding evolution in the morphology of the vascularity of the body-part. For example, a decrease or an increase of the skewness $\gamma$ can be indicative of the effectiveness of an anti-angiogenic or a pro-angiogenic drug treatment, respectively.

In a different embodiment of the invention, the probability density distribution is estimated without making any assumption about its nature. For this purpose, it is necessary to fit the sample vector E'=[ ] by a corresponding model vector M=[M($t_0$), ... M($t_M$)], given by the evaluation of the model function M(t) at the same times $t_j$ (for a vector of predefined transit times $\tau=[\tau_0, \ldots, \tau_N]$); preferably, the transit time vector $\tau[\ ]$ is defined by selecting N values in a given interval of interest, according to an arithmetic or geometric progression.

In order to perform the above-described operation, we define a scaled probability vector $C_A=[C_{A0}, \ldots, C_{AN}]=A \cdot [C_0, \ldots, C_N]$, with $C_{Ai}=A \cdot C_i \geq 0$ and $$\sum_{i=0}^{N} C_{Ai} \cdot (\tau_{i+1} - \tau_i) = \sum_{i=0}^{N} A \cdot C_i \cdot (\tau_{i+1} - \tau_i) = A,$$

and a vector of factors $P=[p_0, \ldots, p_N]$, with $p_i=C_{Ai} \cdot (\tau_{i+1}-\tau_i)$. The model vector M[ ] (assuming the offset parameter O equal to zero for the sake of simplicity) is then a function of the factor vector P[ ] only. Therefore, we can define an error function between the model vector M[ ] and the sample vector E'[ ] in terms of the factor vector P[ ]; for example:

$$err(P) = \sum_{j=0}^{M} |M(P, t_j) - E'(t_j)|.$$

The factor vector P[ ] can be estimated by minimizing the error function err(P), with the constrain that $p_i \geq 0$. Each element of the scaled probability vector $C_A[\ ]$ is then calculated as:

$$C_{Ai}=p_i/(\tau_{i+1}-\tau_i).$$

It is now possible to estimate the amplitude parameter A by applying the above-mentioned formula $$A = \sum_{i=0}^{N} C_{Ai} \cdot (\tau_{i+1} - \tau_i),$$

and then obtain the probability vector $C[\ ]=C_A[\ ]/A$.

This result can be achieved using the interior-reflective Newton method described in Coleman, T. F. and Y. Li, "An Interior, Trust Region Approach for Nonlinear Minimization Subject to Bounds", SIAM Journal on Optimization, Vol. 6, pp. 418-445, 1996 and in Coleman, T. F. and Y. Li, "On the Convergence of Reflective Newton Methods for Large-Scale Nonlinear Minimization Subject to Bounds", Mathematical Programming, Vol. 67, Number 2, pp. 189-224, 1994 (for example, implemented by the Optimization Toolbox of the Matlab® programming language). This technique requires the setting of an initial estimate of the factor vector PD. The choice of the initial estimate of the factor vector P[ ] is rather important, since the error function err(P) may have several local minima that allow finding a good approximation of the perfusion function E(t), but not of the factor vector PD. In this case, excellent results were obtained by setting each element of the factor vector P[ ] as follows:

$$p_i=1/N$$

or $$p_i=(\tau_{i+1}-\tau_i) \cdot [\max(\tau_0, \ldots, \tau_N)-\min(\tau_0, \ldots, \tau_N)].$$

It is now possible to calculate any desired statistics indicator of the probability vector C[ ], such as its mean value, variance and skewness:

$$\tau_{mean} = \frac{\sum_{i=0}^{N} C_i \cdot \tau_i}{N}$$

$$\sigma^2 = \frac{\sum_{i=0}^{N} C_i \cdot (\tau_i - \tau_{mean})^2}{N}$$

$$\gamma = \frac{\sum_{i=0}^{N} C_i \cdot \left(\frac{\tau_i - \tau_{mean}}{\sigma}\right)^3}{N}.$$

Also in this case, the shape indicators so obtained can be used to characterize the morphology of the vascularity of the body-part under analysis. In addition, it is also possible to detect morphological anomalies in the vascularity of the body-part by comparing the estimated probability density distribution with the lognormal function (characterizing healthy tissues).

Experimental tests have shown that the proposed solution provides good results for echo-power signals with low noise; however, when a non-negligible noise is superimposed to the echo-power signals, the accuracy of the results is impaired.

In this case, it has been found advantageous to apply further estimation steps. For example, in an embodiment of the invention a first estimation of the factor vector P[ ] and then of the scaled probability vector $C_A[\ ]$ is obtained as described above for a relatively low first number of transit times N; for example, the first number of transit times N is from 4 to 16, and preferably from 6 to 10 (such as 8). A second estimation of the scaled probability vector $C_A[\ ]$ for a higher second number of transit times N is then extrapolated from the first estimation; preferably, the second number of transit times N is from 8 to 64, and preferably from 16 to 48 (such as 32). For example, this result is achieved by applying a cubic spline interpolation to the first estimation of the scaled probability vector $C_A[\ ]$. In detail, the first estimation of the scaled probability vector $C_A[\ ]$ is fitted by a cubic smoothing spline function in the transit time domain (for example, using the csaps function of the Matlab® programming language). The cubic smoothing spline function is evaluated at the second number of transit times N (for example, again uniformly distributed in the interval of interest). A second estimation of each element of the factor vector P[ ] is then obtained as $p_i = C_{Ai} \cdot (\tau_{i+1} - \tau_i)$.

The second estimation of the factor vector P[ ] is used to initialize a neural network, which performs a third estimation step. As it is well known in the art, a neural network is a data processing system that approximates the operation of the human brain. A neural network consists of basic processing elements (called neurons), which are connected by means of unidirectional channels (called synapses); the neurons (and the corresponding synapses) are organized into one or more layers between an input and an output of the neural network (receiving an input vector IN[ ] and providing an output vector OUT[ ], respectively). The synapsis associated with each k-th neuron receives a corresponding input vector $IN_k[\ ]$ (from other neurons or from the input of the neural network); the synapsis multiplies the input vector $IN_k[\ ]$ by a corresponding weight vector $W_k[\ ]$ and then adds a bias value $b_k$. The resulting vector $W_k[\ ] \cdot IN_k[\ ] + b_k$ in supplied to the associated neuron, which outputs a scalar value $Out_k[\ ]$ according to a predefined transfer function (for example, the sigmoid or identity function):

$$OUT_k[\ ] = g(W_k[\ ] \cdot IN_k[\ ] + b_k).$$

The neural network is initially trained, by providing a large amount of examples (each one consisting of an input vector IN[ ] with the corresponding output vector OUT[ ]); the weight vectors $W_k[\ ]$ and the bias values $b_k$ are iteratively adjusted so as to fit the available examples. For example, the training process is performed by minimizing a performance function consisting of the mean square error (mse) between the output vectors OUT[ ] and the input vectors IN[ ].

In this context, a simple neural network with a single synapsis/neuron (implementing a transfer function equal to the identity function) is used; this element (having a weight vector W[ ] of N elements and a bias values b) receives the input vector IN[ ] and provides the output vector OUT[ ] directly (both of them including M elements). Therefore, the performance function mse( ) to be minimized becomes:

$$mse = \frac{1}{M} \| W[] \cdot IN[] + b - OUT[] \|^2.$$

If the output vector OUT[ ] is set to the sample vector E'=[ ], the weight vector W[ ] is set to the factor vector P[ ], and the input vector IN[ ] is set to a corresponding bolus-perf vector BolusPerf[ ] given by the evaluation of the product between the perf function and the bolus function B(t) at the times $t_j$ (for the transit time vector $\tau[\ ]$), we have the following performance function mse( ) to be minimized:

$$mse = \frac{1}{M} \sum_{j=0}^{M} [P[] \cdot B(t_j) \cdot perf(t_j) + b - E'(t_j)]^2 = \frac{1}{M} \sum_{j=0}^{M} [M(t_j) + b - E'(t_j)]^2.$$

Therefore, the weight vector W[ ] obtained by training the above-described neural network with the bolus-perf function vector BolusPerf[ ] and the sample vector E'[ ] (assuming that the bias value b is kept as close as possible to zero) provides the desired estimation of the factor vector P[ ] (and then of the probability vector C[ ] as well). For this purpose, the weight vector W[ ] is initialized to the above-mentioned second estimation of the factor vector P[ ]. Moreover, in order to satisfy the constraints that the elements of the weight vector W[ ] are positive and that the bias value b is substantially null, they are periodically reset to zero. The period of the reset operation (in terms of number of iterations) is high enough so as to have the performance function mse( ) decrease significantly (during the training process) before its sharp increase caused by the reset operation; empirically observations provided good results with a period higher then 10, better results with a period higher than 25, and even better results with a period higher than 50 (for example, up to 200), such as 100.

The training process ends when the performance function mse( ) falls below a predefined threshold value. In this respect, acceptable results were obtained with a threshold value between 0.01 and 0.001; particularly, in order to maintain a high accuracy of the training process the threshold value may be reduced as the complexity of the probability density distribution increases or as the period of the reset operation decreases. Advantageously, the stopping condition is not verified at each iteration of the training process, but only before any reset operation; therefore, the total number of iterations of the training process will always be a multiple of the period of the reset operation.

For example, this result can be achieved by using the Matlab® programming language. Particularly, the neural network is created with the newlin function; the performance function (defined by the function net.performFcn) is then minimized with the function traingdx. This function implements a gradient descent algorithm in the batch mode (wherein at each iteration the weights and the bias value are updated only after the entire examples have been applied to the neural network); the function also applies a momentum technique (acting as a low-pass filter that allows ignoring local changes) and an adaptive learning technique (which updates a rate of the gradient descent algorithm dynamically).

Figure 7:
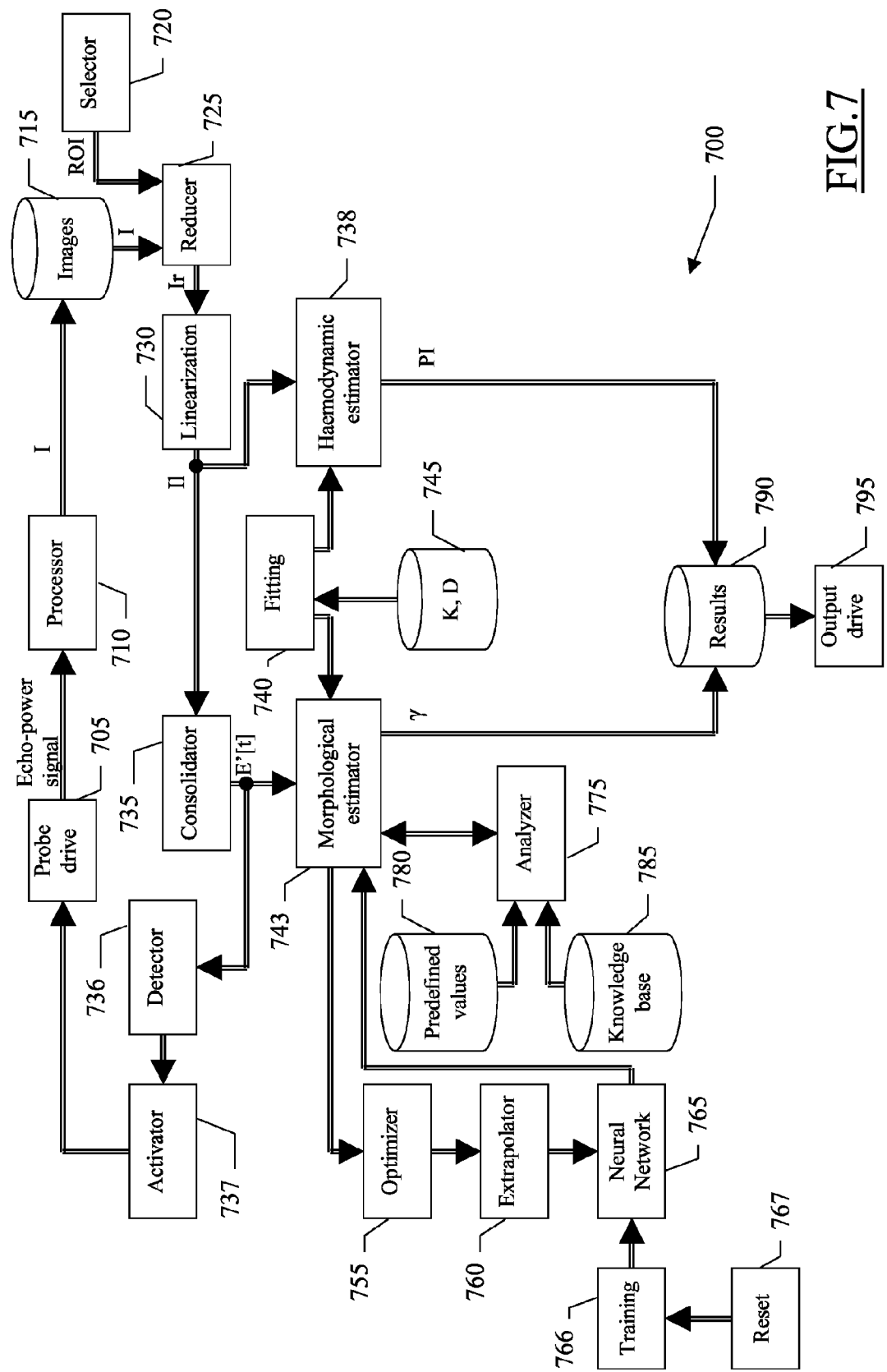
FIG. 7 depicts the main software components that can be used for practicing a perfusion assessment method according to an embodiment of the invention.

Moving now to FIG. 7, the main software components that can be used for practicing a perfusion assessment method according to an embodiment of the invention are denoted as a whole with the reference 700. The information (programs and data) is typically stored on the hard disk and loaded (at least partially) into the working memory when the programs are running, together with an operating system and other application programs (not shown in the figure). The programs are initially installed onto the hard disk, for example, from CD-ROM.

Particularly, a module 705 is used to drive the probe, so as to measure the echo-power signal that is reflected by the body-part being scanned during the perfusion process of the contrast agent; for example, the probe drive 705 includes beam formers and pulsers for generating the ultrasound waves. The measured echo-power signal is supplied to a processor 710. The processor 710 pre-amplifies the echo-power signal and applies a preliminary time-gain compensation (TGC). Typically, the (analog) echo-power signal is then converted into digital values by an Analog-to-Digital Converter (ADC), and combined into a focused signal through a receive beam former. The echo-power signal is also manipulated through digital filters (for example, band-pass filters) and other signal conditioners (for example, post-beam-forming TGC); moreover, the echo-power signal is further manipulated through a demodulator (to extract the amplitude of an echo-envelope) and non-linear conditioners, such as a log compressor (to account for the geometry of the probe). The echo-power signal is optionally compressed again, and then converted into a video format. This process results in a sequence of consecutive images I of the body-part during the perfusion process of the contrast agent, which images I are stored into a corresponding repository 715. Each image consists of a digital representation of the body-part; the image is defined by a matrix (for example, with 512 rows and 512 columns) of visualizing elements, each one representing the intensity of the echo-power signal relating to a basic picture element (pixel) or volume element (voxel).

A selector 720 is used to delimit a region of interest (ROI) for the perfusion process on the images; typically, the ROI identifies a significant portion of the body-part to be analyzed. A mask corresponding to the ROI is applied to the sequence of images I by a reducer 725, so as to obtain a corresponding sequence of reduced images Ir with the information relevant to the perfusion process only. A linearization module 730 processes the sequence of reduced images Ir to make each visualizing element proportional to a local concentration of the microbubbles in the corresponding pixel or voxel; for example, this outcome can be achieved by applying an inverse log-compression and then squaring the values of the visualizing elements so obtained. The resulting sequence of linearized images Il is supplied to a consolidator 735. For each linearized image, the consolidator 735 combines the corresponding visualizing elements into a single value indicative of the acoustic power of the whole ROI at the relevant time; for example, this value is calculated as the average of the visualizing elements. This operation provides the sample vector E'[ ] for the desired ROI; preferably, the consolidator 735 also applies a median filter to the sample vector E'[ ] (for example, implemented by the function medfilt1 of the Matlab® programming language), so as to reduce the negative effect of any noise.

This sample vector E'[ ] is then supplied to a detector 736. The detector 736 determines when the elements of the sample vector E'[ ] reach their absolute maximum value (corresponding to the primary peak of the bolus curve); for example, this result can be achieved by monitoring a gradient of the sample vector E'[ ], so as to detect the reaching of the maximum value when the gradient becomes negative (for a time sufficient to filter out any transient phenomena). The information so obtained is provided to an activator 737, which in response thereto controls the drive probe 705 to apply the destruction pulses. In this way, the destruction pulses are automatically applied just after reaching the primary peak of the bolus curve. Therefore, it is possible to have a good estimation of the bolus curve (since its whole wash-in phase is completed); at the same time, a high amount of contrast agent is still present in the body-part under analysis (so that the resulting echo-power signal provides significant information, its level being far higher than any background noise).

The sequence of linearized images Il is also received by a haemodynamic estimator 738. The module 738 estimates the desired haemodnamic parameter(s) for each pixel or voxel, according to a sample vector E'[ ] defined by the corresponding visualizing elements in the sequence of linearized images Il. For this purpose, the estimator 738 accesses a fitting module 740, which determines the fitting parameters of the model function M(t) when expressed in terms of the reperfusion function E(t) represented as the logperf function. This results in the generation of one or more parametric images PI (associating the value of a corresponding haemodynamic parameter to each pixel or voxel).

Moreover, the sample vector E'[ ] for the whole ROI is supplied by the consolidator 735 to a morphological estimator 743. The module 743 estimates the desired morphological parameters of the selected ROI from the model function M(t) when expressed in terms of the reperfusion function E(t) represented as the continuous or discrete combination of perf functions weighted by the corresponding probability density function $C(\tau)$ or vector of probabilities C[ ], respectively. For this purpose, the estimator 743 can exploit the fitting module 740 to calculate the probability density function $C(\tau)$ when it is assumed to have a lognormal distribution. In this case, the fitting module 740 accesses a table 745 that stores the values K and D, the a priori knowledge of which is typically required. In addition or in alternative, the estimator 743 can also be associated with an optimizer 755, which is used to make the first estimation of the probability vector C[ ]. The first estimation of the probability vector C[ ] is supplied to an extrapolator 760, which determines its second estimation. The second estimation of the probability vector [ ] is in turn passed to a neural network module 765. The neural network module 765 is associated with a corresponding training module 766. A reset module 767 is used to force to zero the weights and the bias value of the neural network periodically. The third estimation of the probability vector C[ ] provided by the neural network module 765 is then returned to the estimator 743. The fitting parameters are then used to calculate the shape indicators for the probability density function $C(\tau)$ or the vector of probabilities C[ ] (for example, its skewness $\gamma$). The morphological parameters so obtained can also be provided to an optional analyzer 775. The analyzer 775, for example, compares the skewness $\gamma$ for the current echo-power signal with one or more predefined values logged in a corresponding repository 780 (typically storing the skewness $\gamma$ obtained for the echo-power signal relating to an alleged healthy body-part, or the skewness $\gamma$ obtained for echo-power signals that were measured previously for the same body-part); in addition, the comparator 775 can access a knowledge base 785, which stores predefined criteria for evaluating the results of the comparison; for example, for each tissue the knowledge base 785 can provide a threshold value of the skewness $\gamma$ (indicative of a healthy condition when not exceeded), can associate different ranges of the skewness $\gamma$ with corresponding pathological conditions, or can establish satisfactory trends of the skewness $\gamma$ over time for different treatments.

The results obtained by the haemodynamic estimator 738 (i.e., the parametric image PI) and/or by the morphological estimator 743 (i.e., on the basis of the skewness $\gamma$) are stored into a file 790. The information stored in the result file 790 is provided to an operator through an output drive 795 (for example, causing its displaying).

Modifications

Naturally, in order to satisfy local and specific requirements, a person skilled in the art may apply to the solution described above many modifications and alterations. Particularly, although the present invention has been described with a certain degree of particularity with reference to one or more embodiments thereof, it should be understood that various omissions, substitutions and changes in the form and details as well as other embodiments are possible; moreover, it is expressly intended that specific elements and/or method steps described in connection with any disclosed embodiment of the invention may be incorporated in any other embodiment as a general matter of design choice.

For example, similar considerations apply if the ultrasound scanner has a different structure or includes other units, or if an equivalent contrast agent is used; likewise, the bolus administration and/or the destruction of the contrast agent can be carried out with similar procedures. Moreover, the principles of the invention should not be limited to the model functions described-above (but they generally apply to whatever model function including the product of any bolus function by any reperfusion function).

In any case, the echo-power signal can be associated to the model function in another way. For example, in an alternative embodiment of the invention the bolus function B(t) alone is estimated (using the echo-power signal taken only in correspondence with an initial portion of the wash-in phase and a final portion of the wash-out phase). The echo-power signal is then divided by the corresponding values of the (estimated) bolus function B(t); this results in a modified sample vector Em'=[Em'($t_0$), ... Em'($t_M$)], with E'm($t_j$)=E'($t_j$)/B($t_j$). In this way, the effects of the bolus administration are substantially removed; therefore, the modified sample vector Em'=[ ] (after the application of the destruction pulses) can now be fitted by the reperfusion function E(t) directly. In this respect, it should be noted that the above-described division (of the sample vector E'=[ ] by the bolus function B(t)) normalizes the amplitude of each element of the modified sample vector Er'=[ ] (and then also of the corresponding reperfusion function E(t)) to unity. In order to restore the actual amplitude of the reperfusion function E(t) (if required), it is necessary to estimate the blood volume in the body-part under analysis. This information can be obtained by calculating the amplitude parameter A as the integral of the bolus function B(t) from $t_0$ to +∞ (given that $$\int_{t_0}^{+\infty} \frac{e^{-\frac{[\ln(t-t_0)-m_B]^2}{2s_B^2}}}{(t-t_o)\cdot s_B\sqrt{2\pi}} dt = 1).$$

The reperfusion function E(t) is then multiplied by the amplitude parameter A so as to restore its actual values. Any desired haemodynamic or morphological indicators can now be estimated as explained in the foregoing. This implementation provides the same results as an embodiment of the invention herein described (even if their accuracy is slightly lower).

Likewise, an embodiment of the proposed solution can be applied to estimate whatever indicator of the perfusion process (either at the pixel/voxel level, at the level of a selected ROI, or at the level of groups of visualizing elements).

Different techniques for linearizing the echo-power signal (to make it proportional to the concentration of the contrast agent in the body-part) are tenable. For example, when dealing with a raw echo-power signal proportional to the acoustic pressure, this result may be achieved simply by squaring the echo-signal amplitude.

In any case, the skewness γ may be calculated with different formulas; moreover, the use of other shape indicators (in addition or in alternative to the skewness γ) is not excluded.

Moreover, the perf function can be defined in an equivalent manner.

Similar considerations apply if the probability density distribution is estimated by means of other techniques for fitting the samples to the model function M(t) (in terms of the reperfusion function E(t) either in the continuous form or in the discrete form); for example, the initial vector of transit times τ[ ] can be selected in another way, the probability vector C[ ] can be estimated directly (instead of the scaled probability vector $C_A$[ ]) by assuming the amplitude parameter A to be the asymptotic value of the sample vector E'[ ]; alternatively, the estimation of the probability vector C[ ] can be performed with a different number of steps (down to a single one), or using other algorithms (for example, based on a wavelet decomposition).

In any case, an embodiment of the invention lends itself to be implemented with a program that is structured in a different way, or with additional modules or functions; likewise, the different memory structures can be of different types, or can be replaced with equivalent entities (not necessarily consisting of physical storage media). Moreover, the proposed solution can implement equivalent methods (for example, with similar or additional steps).

In any case, it is possible to distribute the program in any other computer readable medium (such as a DVD).

Moreover, it will be apparent to those skilled in the art that the additional features providing further advantages are not essential for carrying out the invention, and may be omitted or replaced with different features.

For example, nothing prevents the implementation of the proposed solution with any other reperfusion function (for example, the mono-exponential one).

Moreover, an embodiment of the proposed solution lends itself to be applied even on non-linearized echo-power signals (for example, images), which are not proportional to the concentration of the contrast agent in the body-part. In this case, the reperfusion function is modified by the same process as the one causing the non-linearity (for example, square-root and log-compression).

Likewise, even though in the preceding description reference has been made to the logperf function and to the perf function, this is not to be intended in a limitative manner; indeed, either the reperfusion function or the elementary reperfusion functions can be represented with any other S-shape function, such as the hyperbolic tangent function, the sigmoid function, or any trigonometric or polynomial approximation thereof. For example, possible approximations of the perf function include:

$$perf(q) = sigmoid(2.406 \cdot q)$$

$$perf(q) = \tanh(1.203 \cdot q)$$

$$perf(q) =$$
$$0.5 \cdot [1 + \text{erf}(q)] \cong \text{sign}(q)\left(1 - \frac{1}{1 + a_1|q| + a_2q^2 + a_3|q|^3 + a_4q^4}\right)$$

where sign(q)=1 for q>0 and sign(q)=−1 for q<0, and where $a_1$=0.278393, $a_2$=0.330389, $a_3$=0.000972, and $a_4$=0.078108.

In addition, the estimation of the probability density function C(τ) assuming a distribution other than the lognormal one is not excluded.

In any case, the proposed solution lends itself to be implemented always using a simple bolus function (even in the presence of the recirculation of the contrast agent).

Moreover, the use of equivalent bolus functions (such as a gamma-variate function) may be within the scope of the invention.

The concepts of the present invention may also apply to ultrasound scanners based on different detection schemes or using other measuring techniques.

In any case, the manual triggering of the destruction pulses is contemplated (for example, by an operator that looks at the images on the monitor).

Alternatively, the diagnostic imaging equipment consists of an ultrasound scanner and a distinct computer (or any equivalent data processing system); in this case, the measured data is transferred from the ultrasound scanner to the computer for its processing (for example, through the removable disk, a memory pen/key, or a network connection).

Similar considerations apply if the programs are preloaded onto the hard-disk, are sent to the system through a network, are broadcast, or more generally are provided in any other form directly loadable into the working memory of the system.

At the end, a method according to an embodiment of the present invention lends itself to be carried out with a hardware structure (for example, integrated in a chip of semiconductor material), or with a combination of software and hardware.

The invention claimed is:

1. A perfusion assessment system comprising:
a device configured to:
provide an echo-power signal indicative of a perfusion of a contrast agent in a body part under analysis, the contrast agent being administered as a bolus and undergoing a significant destruction during a passage of the contrast agent in the body part, and
a processor configured to:
associate the echo-power signal to a model function including a mathematical product between a bolus function indicative of the passage of the contrast agent without said destruction and a reperfusion function indicative of a reperfusion of the contrast agent in the body part following the destruction corresponding to a substantially constant inflow of the contrast agent, and
estimate at least one perfusion indicator from the model function, the bolus function, or the reperfusion function.

2. The system according to claim 1, wherein the reperfusion function has an S-shape, the S-shape including an initial portion with substantially zero first derivatives, a final portion with substantially zero first derivatives, and a central portion between the initial portion and the final portion changing monotonically from a value of the initial portion to a value of the final portion.

3. The system according to claim 2, wherein the device is further configured to provide the echo-power signal by processing the echo-power signal to be proportional to a concentration of the contrast agent in the body part.

4. The system according to claim 3, wherein the reperfusion function is a cumulative lognormal function being represented by a set of fitting parameters, and wherein the processor is further configured to estimate the at least one perfusion indicator by deriving the at least one perfusion indicator from the fitting parameters, the at least one perfusion indicator being representative of haemodynamic characteristics of the body part.

5. The system according to claim 3, wherein the reperfusion function is based on a plurality of elementary reperfusion functions with said S-shape each one for a corresponding value of at least one perfusion parameter, the elementary perfusion functions being weighted according to a probability density distribution of the at least one perfusion parameter, and wherein the processor is configured to estimate the at least one perfusion indicator by calculating at least one shape indicator of the probability density distribution, the at least one shape indicator being representative of morphological characteristics of the body part.

6. The system according to claim 2, wherein the reperfusion function is a cumulative lognormal function being represented by a set of fitting parameters, and wherein the estimating comprises deriving the at least one perfusion indicator from the fitting parameters, the at least one perfusion indicator being representative of haemodynamic characteristics of the body part.

7. The system according to claim 2, wherein the reperfusion function is based on a plurality of elementary reperfusion functions with said S-shape, each one for a corresponding value of at least one perfusion parameter, the elementary perfusion functions being weighted according to a probability density distribution of the at least one perfusion parameter, and wherein the processor is further configured to estimate the at least one perfusion indicator by calculating at least one shape indicator of the probability density distribution, the at least one shape indicator being representative of morphological characteristics of the body part.

8. The system according to claim 7, wherein each elementary reperfusion function is a cumulative normal distribution function based on a first predetermined parameter indicative of an echo-power signal measure sensitivity and a second predetermined parameter indicative of a contrast-agent destruction extent.

9. The system according to claim 8, wherein the probability density distribution is a lognormal function of the at least one perfusion parameter and the reperfusion function comprises the integral of the elementary reperfusion functions multiplied by the lognormal function, the lognormal function being represented by a set of fitting parameters, and wherein the processor is further configured to calculate the at least one shape indicator by deriving the at least one shape indicator from the fitting parameters.

10. The system according to claim 8, wherein the probability density distribution is represented by a vector of probabilities, the reperfusion function including the summation of the elementary reperfusion functions multiplied by the corresponding probabilities, and wherein the processor is further configured to calculate the at least one shape indicator by extracting comprises extracting the at least one shape indicator from the vector of probabilities.

11. The system according to claim 7, wherein the probability density distribution is a lognormal function of the at least one perfusion parameter and the reperfusion function comprises the integral of the elementary reperfusion functions multiplied by the lognormal function, the lognormal function being represented by a set of fitting parameters, and wherein the processor is further configured to calculate the at least one shape indicator by deriving the at least one shape indicator from the fitting parameters.

12. The system according to claim 7, wherein the probability density distribution is represented by a vector of probabilities, the reperfusion function including the summation of the elementary reperfusion functions multiplied by the corresponding probabilities, and wherein the processor is further configured to calculate the at least one shape indicator by extracting the at least one shape indicator from the vector of probabilities.

13. The system according to claim 2, wherein the bolus function comprises the sum of a plurality of elementary bolus functions.

14. The system according to claim 1, wherein the bolus function comprises the sum of a plurality of elementary bolus functions.

15. The system according to claim 1, wherein the bolus function and each elementary bolus function is a lognormal function.

16. A diagnostic imaging equipment comprising an ultrasound system for acquiring an echo-power signal, and comprising the perfusion assessment system, according to claim 1.

17. The diagnostic imaging equipment according to claim 16, wherein the device is further configured to detect a reaching of a maximum of the echo-power signal and to trigger the destruction in response to the detection of the reaching of the maximum.

18. A perfusion assessment method including the steps of:
providing an echo-power signal indicative of a perfusion of a contrast agent in a body part under analysis, the contrast agent being administered as a bolus and undergoing a significant destruction during a passage of the contrast agent in the body part,
associating the echo-power signal to a model function including a mathematical product between a bolus function indicative of the passage of the contrast agent without said destruction and a reperfusion function indicative of a reperfusion of the contrast agent in the body part following the destruction corresponding to a substantially constant inflow of the contrast agent, and
estimating at least one perfusion indicator from the model function, the bolus function, or the reperfusion function.

19. A non-transitory computer readable medium comprising instructions, that when executed by processor, cause the method of claim 18 to be performed.

20. A perfusion assessment system comprising:
a device configured to:
provide an echo-power signal indicative of a perfusion of a contrast agent in a body part under analysis, the contrast agent being administered as a bolus and undergoing a significant destruction during a passage of the contrast agent in the body part, and
a hardware structure configured to:
associate the echo-power signal to a model function including a mathematical product between a bolus function indicative of the passage of the contrast agent without said destruction and a reperfusion function indicative of a reperfusion of the contrast agent in the body part following the destruction corresponding to a substantially constant inflow of the contrast agent, and
estimate at least one perfusion indicator from the model function, the bolus function, or the reperfusion function.

* * * * *